United States Patent [19]

Högberg et al.

[11] 3,991,187
[45] Nov. 9, 1976

[54] MEDICINAL COMPOSITIONS AND METHODS OF USE INVOLVING PHOSPHORIC ACID ESTERS

[75] Inventors: Knut Bertil Högberg; Hans Jacob Fex, both of Helsingborg; Bo Göran Fredholm, Nyhamnslage; Torsten Rune Perklev; Sten Gunnar Veige, both of Helsingborg, all of Sweden

[73] Assignee: Aktiebolaget Leo, Helsingborg, Sweden

[22] Filed: May 6, 1974

[21] Appl. No.: 467,057

Related U.S. Application Data

[62] Division of Ser. No. 215,671, Jan. 5, 1972, Pat. No. 3,862,270.

[30] Foreign Application Priority Data

Aug. 17, 1971 United Kingdom............... 38619/71
Nov. 10, 1971 United Kingdom............... 52303/71

[52] U.S. Cl.............................. 424/199; 424/200; 424/204; 424/206; 424/211; 424/212; 424/214

[51] Int. Cl.²............... A61K 31/66; A61K 31/675; A61K 31/685

[58] Field of Search .......... 424/204, 205, 214, 199, 424/212, 200, 206

[56] References Cited

UNITED STATES PATENTS 3,423,487  1/1969  Scheuerer et al................... 260/946
3,851,019  11/1974  Hogberg et al..................... 424/214

*Primary Examiner*—Sam Rosen
*Attorney, Agent, or Firm*—Gordon W. Hueschen

[57] ABSTRACT

Novel symmetrical secondary phosphoric acid esters having the general formula

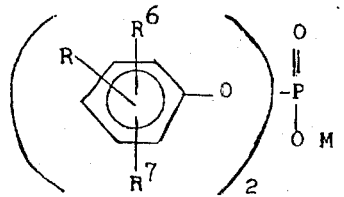

wherein the substituent R is positioned in meta or para position relative to the phosphoric acid ester group; processes for the preparation of said esters; and compositions containing said esters. The esters are i.a. useful as selective inhibitors of prostaglandins and compounds with prostaglandin activities. They also selectively antagonize the slow reacting substance (SRS).

46 Claims, No Drawings

MEDICINAL COMPOSITIONS AND METHODS OF USE INVOLVING PHOSPHORIC ACID ESTERS

This application is a division of our prior-filed co-pending application Ser. No. 215,671, filed Jan. 5, 1972, now U.S. Pat. No. 3,862,270, issued Jan. 21, 1975.

The present invention relates to secondary phosphoric acid esters having valuable pharmacological properties, as well as processes for the preparation thereof. They have all strong activity as selective inhibitors of prostaglandins or compounds with prostaglandin activities. They also selectively antagonize the slow reacting substance (SRS), an unsaturated hydroxy-acid of lipid nature related to the prostaglandins. (Cf. Acta Physiol.Scand. 82 1971, p. 358 by Strandberg K. and Uvnas B). Like many substances with receptor blocking properties, e.g. certain adrenergic $\beta$-blocking agents, the compounds of this invention also exert intrinsic in this case smooth muscle stimulatory activity. These esters are also useful as surface active agents and as additives in extractions of cations due to the presence of both hydrophilic and lipophilic groups in the same molecule. They also exert corrosion-inhibitory effects.

The prostaglandins (PG) are a new group of biologically active substances affecting many important physiological processes and also influencing intracellular metabolism. See e.g. reviews as those from S. Bergström et al. in Pharmacol. Rev. 20 (1968) 1 and P. W. Ramwell and J. E. Shaw in "Recent progress in hormone research" vol. 26 (1970) p. 139.

Evidence that prostaglandins are involved in a large number of physiological and pathological processes is rapidly accumulating. Two major areas where these compounds play an important physiological role are the control of fertility and the regulation of blood flow. Further, the prostaglandins have potent pharmacological actions on smooth muscle in various other organs such as the gastrointestinal and the respiratory tracts. They are also involved in the events following nerve stimulation, both centrally and in the periphery, as well as in the process of lipolysis.

In the area of reproduction prostaglandins are involved in several ways. It is known, for instance, that sufficient amounts of prostaglandins to affect the female genital-tract smooth muscles are delivered with the semen and thereby probably promote conception. At full term the levels of prostaglandins in plasma and amniotic fluid are increased which in turn initiates the onset of labour. This latter effect of prostaglandins is presently being used therapeutically.

The circulatory effects of prostaglandins are as a rule vasodepressor, although PGF in some instances may cause a rise of the blood pressure. The way in which prostaglandins normally contribute to blood-flow regulation has not yet been elucidated.

In the gastrointestinal tract prostaglandins generally cause contraction of the smooth muscle. Certain kinds of diarrhoea are believed to be caused by high plasma levels of prostaglandins. In the lungs PGF causes bronchoconstriction while PGE has the opposite effect. At nerve stimulation prostaglandins are released and, at least in peripheral nerves, seem to counteract the result of the stimulation.

The effects of prostaglandins are generally obtained with very small amounts of the compounds, and this observation, together with the fact that prostaglandins are widely distributed in the organism point to an important role of these compounds in homeostatic mechanisms. However, although so many important pharmacological effects of prostaglandins are known, the exact nature of their physiological involvement is poorly understood. This is in part due to the fact that no suitable inhibitory compound has so far been available.

Having very pronounced physiological and pharmacological effects the prostaglandins could safely be anticipated also to play an important role in pathological conditions. Accordingly, there is now rapidly growing evidence for this, a fact that further emphasizes the need for prostaglandin-inhibitory agents. Thus, prostaglandins are involved in inflammatory processes of various kinds, such as burns, contact debmatitis and anaphylactic reactions. In these cases prostaglandins have been suggested to be mediators of the reaction. One important condition, for example, in which prostaglandins are considered to be of etiological significance, is bronchial asthma. In this connection it is of interest to mention that a substance, chemically and pharmacologically closely related to the prostaglandins, namely Slow Reacting Substance (SRS), is also produced during anaphylaxis, e.g. in bronchial asthma. A possibility to counteract the effect of this substance is thus also highly desirable.

Against the background of the above information it is evident that major therapeutic advances may result from the use of prostaglandin-inhibitory substances. Inhibition of various inflammatory reactions, improvement of bronchial asthma, regulation of blood flow, control of gastrointestinal hypermotility are a few examples of expected therapeutic effects of such compounds. With increasing knowledge about the functions of prostaglandins the usefulness of inhibitors therefor will no doubt become still more apparent. Not only will conditions characterized by an increased formation of prostaglandins be improved, but it is already possible to influence certain physiological processes when desired, such as for example the conception.

The basic chemical structure of the PG:s is a $C_{20}$ fatty acid, prostanoic acid, containing a five-membered ring.

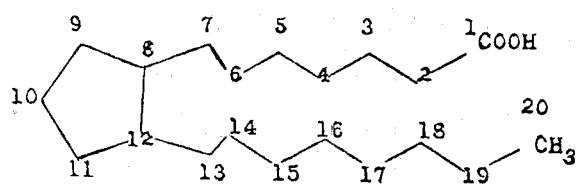

Depending on the substituents in the five-membered ring four different abbreviations are used in the literature.

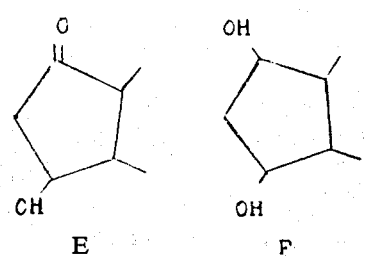

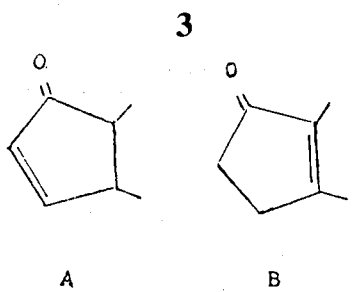

A  B

All E-types prostaglandins have 11α-hydroxy and 9-keto groups in the cyclopentane ring. In the F-types the 9-keto group is reduced to a (α or β) hydroxyl group. All the "primary" prostaglandins contain a 13:14 trans double bond. $E_1$ and $F_1$ compounds have only this one double bond the $E_2$ and $F_2$ molecules have an additional 5:6 cis double bond and the $E_3$ and $F_3$ a further cis double bond between 17 and 18. All naturally occurring prostaglandins found to-day have a 15(S)-hydroxy group. 9α, 11α, 15(S)-tri hydroxy-5-cis, 13-trans-prostadienoic acid has for example, been called prostaglandin $F_{2\alpha}$ and further abbreviated as $PGF^{2\alpha}$.

Details about the chemistry of the prostaglandins are found, e.g. in a review by P. W. Ramwell et al, in "Progress in the chemistry of fats and other lipids" vol. IX, p. 231.

It is also known that compounds with a structure related to the naturally occurring prostaglandins can hve similar effects. See e.g. P. W. Ramwell et al. in Nature 221 (1969) 1251 and W. Lippman in J. Pharm. Pharmacol. 22 (1970) 65.

Some antagonists of prostaglandins have already been described. J. Fried et al., Nature 223 (1969) 208, found that 7-oxa-prostaglandin-like compounds with 6-membered rings inhibited prostaglandin $E_1$ ($PGE_1$).

A derivative of dibenzoxazepine was found to antagonize $PGE_2$ (J. H. Sanner in Arch. int. Pharmacodyn. 180 (1969) 46).

A high molecular weight polyester between phloretin and phosphoric acid was also found to have a prostaglandin-blocking activity. (K. E. Eakins et al. Brit. J. Pharmac. 39, (1970) 556); and in addition to be an antagonist of slow reacting substance (abbreviated SRS) (Mathe, A. A., and Strandberg, K. in Acta physiol. scand. 82 (1971) 460).

This polymer, polyphloretin phosphate, was already described by E. Diczfalusy et al. in Acta Chem. Scand. 7 (1953) 913, as a cross-linked high molecular weight enzyme inhibitor. It has an average molecular weight of 15 000, did not dialyze through a cellophane membrane, and was found to be a strong inhibitor of various enzymes e.g. hyaluronidase and alkaline phosphatase.

These materials are complex mixtures of various different polymeric structures in varying proportions (due to the inability to control either the degree of polymerisation or selectivily induce such polymerisation at specific reaction sites in view of the availability of numerous possible sites at which polymerisation can occur) and the activity which has been attributed thereto could not be attributed to any specific polymeric structure, much less any specific molecular weight fraction of any certain structures or units thereof, either in theory or in practice, in which latter aspect positive identification of specific active components of the complex polymeric mixture has been impossible.

It has now, surprisingly, been found that certain simple synthetic secondary phosphoric acid esters of the structures shown below are very good selective inhibitors of prostaglandins and compounds with prostaglandin activities and that they also selectively antagonize the slow reacting substance (SRS). These effects are shown in examples No. 19, and No. 22 respectively.

In addition the esters of this invention exert a smooth muscle stimulatory activity as demonstrated in examples Nos. 17, 20 and 21.

Since the compounds of the invention are produced synthetically, they have a definitive structure and are of course substantially free of inactive or lesser active impurities and materials of similar and/or indefinite composition and structure.

In the types of experiments described by Eakins et al (ibid.) most of the compounds are much stronger inhibitors against prostaglandins, e.g. $E_1$ ($PGE_1$), $E_2$ ($PGE_2$), $F_{1\alpha}$ ($PGF_{1\alpha}$) and $F_{2\alpha}$ ($PGF_{2\alpha}$) than polyphloretin phosphate and they are also superior as antagonists for slow reacting substance (SRS) in the types of experiments described by Mathe and Strandberg (ibid). In addition the phosphoric acid esters of this invention have no such antienzymatic properties as those described for this polymer.

The expression "prostaglandins" (PG:s) as used in this disclosure is intended to cover prostaglandins and related structures as indicated above of natural as well as synthetic origin.

Accordingly, one object of the invention is to provide new compounds possessing activity as selective inhibitors of prostaglandins or compounds with prostaglandin activities.

Another object of the invention is to provide new compounds possessing activity as selective inhibitors of the slow reacting substance (SRS).

Still another object of the invention is to provide new compounds with a smooth muscle stimulatory effect.

A further object of the invention is to provide a method of treating an animal body to produce a prostaglandin inhibitory effect.

Yet another object of the invention is to provide a method of treating an animal body to produce an antagonizing effect of the slow reacting substance (SRS).

Yet another object of the invention is to provide a method of treating an animal body to produce a smooth muscle stimulatory effect.

According to the invention there are provided symmetrical secondary phosphoric acid esters having the general formula

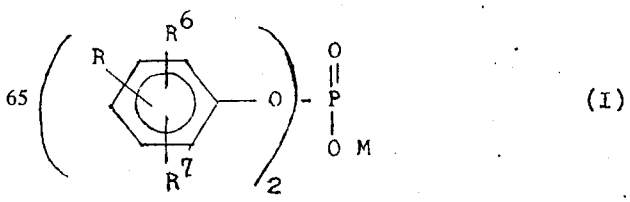

(I)

or functional derivatives thereof wherein the substituent R is positioned in meta or para position relative to the phosphoric acid ester group. The substituent R is

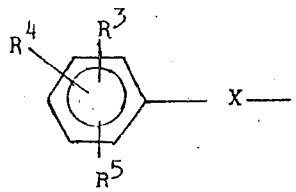

wherein the group X is

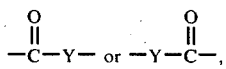

wherein Y is a straight hydrocarbon chain having 2 or 3 carbon atoms and being saturated or containing one double bond. At most 2 hydrogen atoms of Y may be substituted by substituents selected from lower alkyl, lower alkenyl, cyano, phenyl, phenyl substituted in p-position by lower alkyl, lower alkoxy, halogen (F, Cl, Br) or $CF_3$, benzyl, and benzyl substituted in p-position by lower alkyl, lower alkoxy, halogen (F, Cl, Br) or $CF_3$. The keto group of X may also be in the form of a conventional aliphatic ketal. $R^3$, $R^4$, $R^5$, $R^6$ and $R^7$ are the same or different and are hydrogen; lower alkyl; lower alkenyl; lower alkoxy; hydroxy; hydroxy esterified with phosphoric acid;

$OCOR^8$; F; Cl; Br; $CF_3$; CN; $NO_2$; $COOR^9$; $CH_2COOR^9$; $OCH_2COOR^9$; $CONR_2^8$; $CH_2CONR_2^8$; $OCH_2CONR_2^8$; $NR_2^8$; $CNR^8COR^8$; $CH_2NR_2^8$; $CH_2NR^8COR^8$; wherein $R^8$ is selected from the group consisting of hydrogen and lower alkyl, and wherein $R^9$ is selected from the group consisting of hydrogen, lower alkyl and M, where M is selected from the group consisting of H; Na; K; ½ Ca and a pharmaceutically acceptable amine.

Among pharmaceutically acceptable organic cations those derived from the following amines may be mentioned: Monoethanolamine, diethanolamine, dimethylaminoethanol, N-methylglucamine, trishydroxymethylmethylamine, morpholine or the like. In this disclosure the expression "lower" means that the group referred to contains one to four carbon atoms, inclusive. Thus, lower alkyl, lower alkenyl and lower alkoxy include for instance: methyl, ethyl, propyl, iso-propyl, butyl, secondary butyl, iso-butyl, tertiary butyl, vinyl, iso-propenyl, 1-propenyl, alkyl, methoxy, ethoxy, propoxy, isopropoxy, isobutoxy, secondary butoxy, tertiary butoxy.

Among the compounds covered by the above general formula (I) those, wherein Y is a substituted or unsubstituted straight hydrocarbon chain having two carbon atoms are preferred. Among these, particularly those, wherein the carbon atom adjacent to the keto-group of X is substituted are of particular interest. The substitution may consist in one or two lower alkyl groups or one aryl group.

With regard to substituents $R^3$, $R^4$, $R^5$, $R^6$ and $R^7$ it is preferred that at least two of said substituents are hydrogen. However, it is also preferred that at least one of said substituents is different from hydrogen.

If in the compounds of the present invention at least one of substituents $R^3$, $R^4$, $R^5$, $R^6$ and $R^7$ is hydroxy or a derivative thereof, namely lower alkyl ethers or esters with lower alkanoic acids. The preferred position of such substituent or substituents is o-position relative to the keto-group of X. This is the case also when one of said substituents contains an amino group, which may be in the form of an amide of a lower alkanoic acid.

If one of substituents $R^3$, $R^4$ and $R^5$ is derived from a carboxylic acid or derivative thereof, namely an amide or an ester of a lower alcohol, such substituent is preferably positioned in p- or m-position relative to X.

In those compounds, wherein R is positioned in m-position relative to the phosphoric acid ester group, useful compounds are also obtained when $R^6$ and $R^7$ are both hydrogen.

Another group of preferred compounds are those, wherein at least one of substituents $R^3$, $R^4$ and $R^5$ is hydroxy or a derivative thereof and X is

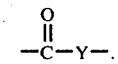

If such hydroxy substituent is positioned in m- or p-position relative to X, esterification of such hydroxy group with phosphoric acid confers water solubility to the compounds hereby obtained.

One group of compounds of interest are those, wherein R is positioned in p-position relative to the phosphoric acid ester group and wherein one of substituents $R^3$, $R^4$ and $R^5$ in m- or p-position relative to X contains an amino-group, which may be in the form of an amide of a lower alkanoic acid, at least one of $R^6$ and $R^7$ being lower alkyl or lower alkoxy. If, however, with the same proviso, with regard to $R^3$, $R^4$ and $R^5$, R is positioned in m position relative to the phosphoric acid ester group, $R^6$ and $R^7$ may both be hydrogen, among the compounds covered by the general formula (I), those are particularly preferred, wherein M is selected from the group consisting of Na, K, ½ Ca, diethanolamine, dimethylaminoethanol, N-methylglucamine and morpholine.

The compounds having the above formula (I) may be prepared by methods known per se, see for instance Houben Weyl. Methoden der organischen Chemie, IV Ed. Vol. XII/2, p. 226. Among such methods for instance the following are useful:

PREPARATION OF COMPOUNDS (I) ABOVE a. A compound having the formula

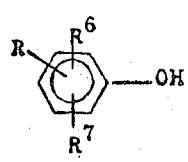

(II)

having only one free hydroxy group is allowed to react with about 0.5 mole of phosphorus oxychloride, suitably in the presence of a tertiary amine, for instance pyridine. After the esterification unreacted chlorine atoms are hydrolyzed with water and the secondary ester obtained corresponding to the above formula 1 is isolated from the reaction mixture in the form of a free acid or as a suitable salt thereof.

If only 0.3 – 0.4 mole of phosphorus oxychloride is used a great number of corresponding tertiary phosphoric acid esters may also be formed. Such esters can be hydrolyzed, for instance with alkali, to give the desired secondary esters corresponding to formula I.

b. A compound having the formula II above and containing only one free hydroxy group is allowed to react with 0.5 mole of trichloroethyl phosphorodichloridate, $Cl_3CCH_2OP(O)Cl$, in the presence of a tertiary amine, e.g. pyridine. When both chlorine atoms of said chloridate have reacted the tertiary phosphoric acid obtained is treated with for instance Zn in pyridine-acetic acid or Zn/Cu in dimethylformamide to remove the trichloroethyl ester group resulting in a secondary phosphoric acid ester having the formula I.

c. A compound of formula II containing only one free hydroxy group is allowed to react with 0.5 mole of methylphosphoramidic dichloride in an inert organic solvent, for instance benzene, and in the presence of at least one mole of a tertiary amine, for instance triethylamine. The reaction may also be carried out using a suitable amine, for instance pyridine, as solvent. The bis-II N-methylphosphoramidate obtained is then hydrolyzed in an acidic solution, e.g. containing formic acid or sulfuric acid, giving a secondary phosphoric acid ester having formula I.

d. A primary phosphoric acid ester derived from a compound having the formula II thus having the general formula:

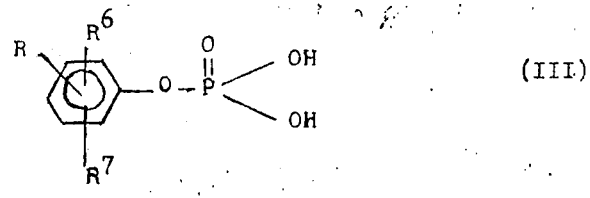

(III)

is allowed to react in an activated form with about one mole of the corresponding compound having formula II. This reaction may for instance be carried out in the presence of about 2 moles of 2,4,6-triisopropylbenzenesulphonyl chloride and about 2 moles of a tertiary amine, e.g. triethylamine, using a suitable solvent, for instance pyridine. After the condensation has been completed water is added making it possible to isolate the symmetrical secondary phosphoric acid having the formula I.

e. The compounds having formula I of the invention may also be prepared by hydrolyzing diphosphoric acid tetraesters prepared in a manner known per se, for instance according to the schematic reaction sequence indicated below

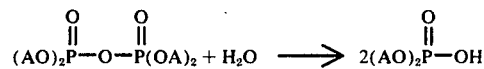

wherein A =

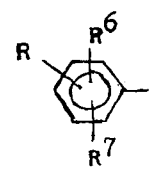

f. The compounds having formula I according to the instant invention may also be prepared by converting, in a manner known per se, derivatives thereof, for instance a phosphoric acid diester amide or a phosphoric acid diester halogenide, to secondary phosphoric acid esters of formula I. This may be illustrated by the following reaction formulas, wherein A has the meaning described under e. above.

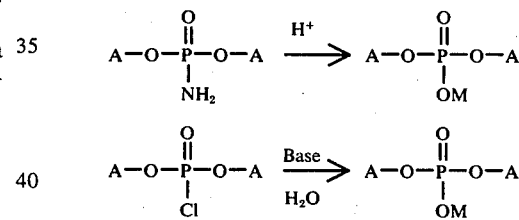

g. It is also possible to prepare the compounds according to the present invention by first preparing a secondary phosphoric acid ester, wherein one or several of the substituents $R^1, R^2, R^3, R^4, R^5, R^6, R^7, R^8$ and $R^9$ consist of other groups than those desired, and then converting such groups in a manner known per se into the groups defined by the general formula I.

b. It is also possible in a manner known per se to prepare compounds having the general formula I from other compounds within the definition of the general formula I.

i. The compounds having formula I of the invention may also be prepared by using 2-chloromethyl-4-nitrophenyl phosphorodichloridate in the reaction steps shown below wherein A has the meaning described under e. above.

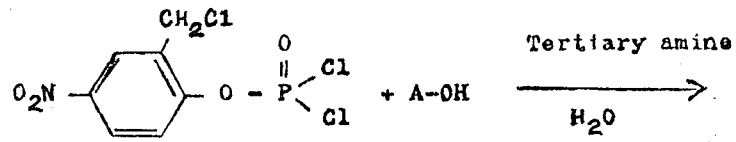

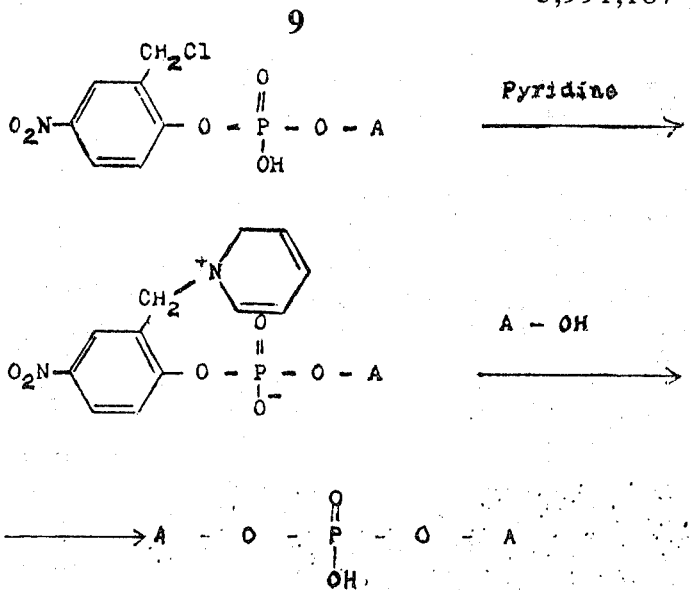

j. The compounds having formula I of the invention may also be prepared by the method described by J. Reiss in Bull. Soc. Chim. France 1965 p. 29 from a primary phosphoric acid ester of A according to the reaction steps shown below wherein A has the meaning described under e. above.

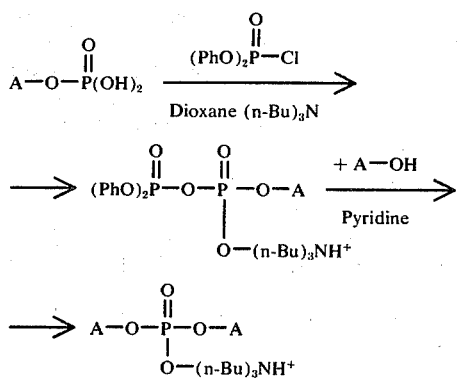

If the secondary phosphoric acid esters having the above formula I are isolated in the form of the free acids, such acids can be transferred to a salt with a pharmaceutically acceptable inorganic or organic cation in a conventional way. Examples of suitable inorganic cations are sodium, potassium and calcium. When a secondary phosphoric acid ester according to this invention is isolated in the form of a salt with a cation which is not pharmaceutically acceptable such salts are transferred to the free acids or to salts of pharmaceutically acceptable cations according to methods known per se, for instance by treatment of a salt with a strong acid, by using a suitable ion exchanger or by carrying out a double decomposition in a suitable solvent.

The method used when synthesizing the secondary phosphoric acid esters of the invention have to be chosen in such a way, that all groups in the starting materials involved are compatible with the method used or, if necessary, sensitive groups are protected during the reaction and then converted to the desired groups so that the compound of the general formula I is obtained. The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in anyone of various ways, for example orally as in capsules or tablets, or parenterally in the form of sterile solutions, suspensions, or by pellet implantation. Among possible routes of parenteral administration are intravenously, subcutaneously, intramuscularly and intraperiotoneally. Other modes of administration are lingually, vaginally, by aerosol and topically as e.g. in the form of ointments, eye-drops etc.

As representative of living animal bodies which may be treated with the compounds and compositions of the invention, and according to the method of treating of the invention, for alleviation of the same and/or similar conditions as those described, in addition may also be mentioned the following: domestic animals such as dogs and cats, farm animals such as horses, cows, sheep and goats.

Pharmaceutical formulations are usually prepared from a predetermined quantity of one or more of the compounds of the invention. Such formulations may take the form of powders, suppositories, ointments, eye-drops, elixirs, solutions, aerosols, pills, capsules, pellets or tablets, suspensions, oil solutions etc., with or without, but preferably with, any one of a large variety of pharmaceutically acceptable vehicles or carriers. When in admixture with a pharmaceutical vehicle or carrier, the active ingredient usually comprises from about 0.01 to about 75 per cent, normally from about 0.05 to about 15 per cent, by weight of the composition. Carriers such as starch, sugar, talc, commonly used synthetic and natural gums, water, and the like, may be used in such formulations. Binders such as polyvinylpyrrolidone and lubricants such as sodium stearate, may be used to form tablets. Disintegrating agents such as sodium bicarbonate may also be included in tablets.

Although relatively small quantities of the active materials of the invention, even as low as 5.0 milligram, may be used in cases of administration to subjects having a relatively low body weight, unit dosages are preferably 5 milligrams or above and preferably 25, 50, or 100 milligrams, or even higher, depending of course upon the subject treated and the particular result desired, as will be apparent to one skilled in the art. Broader ranges appear to be 0.1 to 3.000 milligrams per unit dose. The active agents of the invention may be combined fo administration with other pharmacologically active agents, such as natural or synthetic prostaglandins or analogous, antiseptics, spasmolytics, analgestics, tranquillizers, steroids or hormones, or the like, or with bufferts, antacids or the like, and the proportion of the active agent of agents in the compositions may be varied widely. It is only necessary that the active ingredient of the invention constitutes an effective amount, i.e., such that a suitable effective dosage will be obtained consistent with the dosage form employed. Obviously, several unit dosage forms may be administered at about the same time. The exact individual dosages as well as daily dosages in a particular case will of course be determined according to well established medical and/or veterinary principles. As a rule, however, when used therapeutically, the present compounds may be administered in a quantity of 1 to 1000 milligrams per day and patient, divided in 1 to 4 doses, during a period of 1 day to 1 year.

The following examples are intended to illustrate but not to limit the scope of the present invention.

EXAMPLE 1.

2.91 g of 4'-chloro-3-(4-hydroxy-3-methoxyphenyl)-propiophenone dissolved in 12 ml pyridine is slowly added (10 min) with stirring to a solution of 0.46 ml phosphorus oxychloride in 5 ml pyridine at a temperature of −20°. The reaction mixture is kept at −5° for 2 h and then at room temperature for an additional 70 h. Water is then added and the resulting solution poured into a separatory funnel containing a mixture of 2.5 M hydrochloric acid (100 ml) and ethyl acetate (100 ml). The organic phase is washed with water and saturated disodium sulfate solution. The ethyl acetate solution is dried with disodium sulfate, filtered and evaporated in vacuo and the residue chromatographed on silica gel. The small amount of tertiary phosphate ester present is eluated with ethyl acetate. The secondary ester is then eluated with ethyl acetate : methanol (1:9) collected and evaporated in vacuo. The residue is dissolved in acetone : water (1:4) with sodium hydroxide to a pH-value of about 4. Most of the acetone is removed in vacuo and the remaining water solution freeze-dried. The salt obtained is sodium bis(4-(3-(4-chlorophenyl)-3-oxopropyl)-2-methoxyphenyl) phosphate which is pure according to TLC and has the following structure

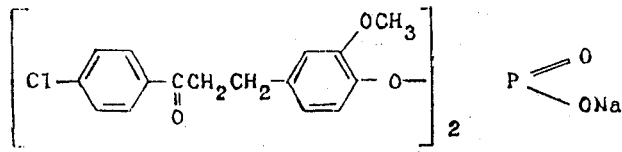

In a similar manner the sodium salt of the following symmetrically secondary phosphoric acid esters are obtained starting from phosphorus oxychloride and a corresponding monophenolic compound being a substituted chalcone or dihydrochalcone with the free phenolic hydroxy group situated in one of the two benzene rings of the chalcone- or dihydrochalcone- skeleton and always in a position not ortho to the carbon-chain between these two benzene rings. The different substituted chalcones and dihydrochalcones, which are used as starting material together with phosphorus oxychloride will be clearly understood from the names of the endproducts mentioned below.

sodium bis(2-methoxy-4-(3-(2-nitrophenyl)-3-oxopropenyl)phenyl)phosphate
sodium bis(2-methoxy-4-(3-nitrophenyl)-3-oxopropenyl)phenyl) phosphate
sodium bis(2-methoxy-4-(3-(4-nitrophenyl)-3-oxopropenyl)phenyl) phosphate
sodium bis(2-methoxy-4-(3-oxo-3-(3-trifluoromethyl)-phenyl)propyl)-phenyl) phosphate
sodium bis(5-(3-(4-fluorophenyl)-3-oxopropenyl)-2-methoxyphenyl) phosphate
sodium bis(2-methoxy-4-(3-(4-cyanophenyl)-3-oxopropenyl)phenyl) phosphate
sodium bis(4-(3-(4-ethoxycarbonylphenyl)propionyl)-2-methoxyphenyl) phosphate
sodium bis(2,3-dimethyl-4-(3-(4-methoxyphenyl)-3-oxopropyl)-phenyl) phosphate
sodium bis(2,5-dimethyl-4-(3-(4-methoxyphenyl)-3-oxopropyl)-phenyl) phosphate
sodium bis(3-ethyl-2-methoxy-4-(3-(4-methoxyphenyl)-3-oxopropyl)phenyl) phosphate
trisodium bis(3-(3-(4-carboxylatomethylphenyl)-3-oxopropyl)phenyl) phosphate
sodium bis(3-(3-(4-methoxycarbonylmethylphenyl)-3-oxo-propyl)phenyl) phosphate
sodium bis(3-(3-(4-(N,N-dimethylcarbamoylmethyl)-phenyl)-3-oxopropyl)phenyl) phosphate
sodium bis(5-(3-(4-chlorophenyl)-3-oxopropyl)-2-methoxyphenyl) phosphate
sodium bis(3-(3-(4-cyanophenyl)acryloyl)phenyl) phosphate
trisodium bis(3-(3-(4-carboxylatophenyl)propionyl)-phenyl) phosphate
sodium bis(3-(3-(4-(acetamidomethyl)phenyl)propionyl)phenyl) phosphate
trisodium bis(4-(3-(4-carboxylatophenyl)-2-(4-methoxy-phenyl)-acryloyl)-3-methoxyphenyl) phosphate
sodium bis(3-(1-cyano-3-(4-methylphenyl)-3-oxopropyl)phenyl) phosphate

EXAMPLE 2

A solution of 2 g triethylamine in 20 ml dry benzene is slowly added (20 min) to a refluxing solution of 1.5 g N-methylphosphoramidic dichloride and 5.08 g of 2',4'-dimethyl-3-(4-hydroxyphenyl)propiophenone in 40 ml dry benzene. Heating is continued for another hour. After cooling the precipitated triethylamine hydrochloride is removed by filtration and the benzene solution washed with dilute hydrochloric acid, sodium hydrogen carbonate solution and water. After drying over anhydrous sodium sulfate the benzene is removed by evaporation in vacuo. The amidate obtained is heated under reflux in 50 % aqueous formic acid for 1 hour. The solvents are evaporated to dryness in vacuo. The residual oil is dissolved in ethyl acetate and the solution washed with saturated sodium sulfate solution and finally water. After evaporation in vacuo an oil is obtained which after chromatography on silica gel (ethylacetate) gives bis(4-(3-(2,4-dimethylphenyl)-3-oxo-propyl)phenyl)hydrogen phosphate.

In a similar manner there are obtained bis(4-(2-butyl-3-phenylpropionyl)phenyl) hydrogen phosphate
bis(4-(2-ethyl-3-phenylpropionyl)phenyl) hyrogen phosphate
bis(3-(2,3-diphenyl-3-oxopropyl)phenyl) hydrogen phosphate
bis(3-(2-benzoyl-3-(4-chlorophenyl)propyl)phenyl) hydrogen phosphate from N-methylphosphor-amidic dichloride and 2-benzyl-4'-hydroxyhexanophenone, 2-benzyl-4'-hydroxybutyrophenone, 3-(3-hydroxyphenyl)-2-phenyl-propiophenone and 2-(4-chlorobenzyl)-3-(3-hydroxyphenyl)-propiophenone respectively.

EXAMPLE 3

6.3 g of sodium bis(5-(3-(4-fluorophenyl)-3-oxopropenyl)-2-methoxyphenyl phosphate in 75 ml ethanol is hydrogenated with hydrogen at room temperature and atmospheric pressure with 0.3 g of 10 % Pd/C as catalyst. The reaction almost stops when the calculated amounts of hydrogen has been absorbed. The catalyst is removed by filtration and the solvent is evaporated. The residue is precipitated with ether. Yield 6.1 g of sodium bis(5-(3-(4-fluorophenyl)-3-oxopropyl)-2-methoxyphenyl) phosphate.

In the same manner the following compounds are obtained from the nitrosubstituted phosphate esters in Examples 1 and 13.

sodium bis(4-(3-(2-aminophenyl)-3-oxopropyl)phenyl) phosphate
sodium bis(4-(3-aminophenyl)-3-oxypropyl)phenyl) phosphate
sodium bis(4-(3-(4-aminophenyl)-3-oxopropy)phenyl) phosphate
sodium bis(4-(3-(4-aminophenyl)propionyl)-3-methoxyphenyl) phosphate
sodium bis(3-(3-(2-aminophenyl)-3-oxopropyl)phenyl) phosphate The nitro-groups in the starting materials are here reduced to amino-groups at the same time as the doublebonds are hydrogenated.

EXAMPLE 4

To a solution of 5.36 g of 3', 5'-dimethyl-4'-hydroxy-4-phenylbutyrophenone in dry pyridine (20 ml) 2.66 g of freshly distilled trichloroethyl phosphorodichloridate is added with stirring at a temperature of about −15°. The temperature of the resulting reaction mixture is then allowed to rise to room temperature and kept at this level for another 70 h. Water is then added and the resulting mixture poured into a mixture of ethyl acetate and 1 M hydrochloric acid. The ethyl acetate solution is then washed with 0.5 m hydrochloric acid, water, 0.5 M sodium bicarbonate solution and finally with water. After drying over anhydrous sodium sulphate the ethyl acetate is removed in vacuo. The resulting oil is dissolved in 50 ml of a mixture of pyridine - acetic acid (8:2). At a temperature of 0° activated Zn (J. Biol. Chem. 230 (1958) 447; J. Org. Chem. 29 (1964) 2048) is added with stirring. After ½ hour at 0° the temperature is allowed to rise to room temperature. The next day the reaction mixture is filtered and the clear solution obtained poured in 2 M hydrochloric acid. Ethyl acetate is added and the water solution discarded. The ethyl acetate solution is washed with water and dried with disodium sulfate. The solvent is evaporated under vacuum. The residue is dissolved in methanol. Water is added and the precipitate formed collected and dissolved in methanol. Water is added. The precipitate now formed is bis(2,6-dimethyl-4-(4-phenylbutyryl)-phenyl) hydrogen phosphate showing one spot in TLC (silica gel, n-butanol : water).

In a similar manner there is obtained bis(2,6-dimethyl-4-(3-phenylpropionyl)phenyl hydrogen phosphate from trichloroethyl phosphorodichloridate and 3', 5'-dimethyl-4'-hydroxy-3-phenyl-propiophenone.

EXAMPLE 5

A solution of 3'-benzoyloxy-3-(4-hydroxy-3-methoxyphenyl)propiophenon (40.6 g) in 120 ml of anhydrous pyridine is added over two hours to a solution of phosphorus oxychloride (4.6 ml) in 50 ml of pyridine at −20°. The mixture is kept for 2 hours at −5°, for 60 hours at room temperature, for 1 hour at 70°–80° and then cooled to room temperature. Water is added until the solution becomes opalescent. The mixture is stirred over night and then added to a mixture of 1000 ml of 2.5 M hydrochloric acid and about 400 ml of ethyl acetate. The organic phase is washed with water and a saturated sodium sulfate solution and dried with sodium sulfate. The solvent is evaporated and the residue is chromatographed on silica gel. The fraction containing bis(4-(3-(3-benzoylphenyl)-3-oxopropyl)-2-methoxyphenyl) hydrogen phosphate, as checked with TLC, is collected and the solvent evaporated. The residue is dissolved in acetone and 80 ml of 2M sodium hydroxide in 210 ml MeOH is added. After 20 min pH is adjusted to 3 with hydrochloric acid. Water is added until the solution becomes opalescent and the mixture is steam distilled. The residue is decanted, cooled to 0° and filtered. The collected solid is mixed with ethyl acetate and 0.2 M hydrochloric acid. The organic phase is washed with a saturated sodium sulfate solution. The residue after evaporation is dissolved in acetone : water, and pH is adjusted to 4 with sodium hydroxide. The acetone is evaporated and the remaining solution freeze-dried, giving sodium bis(4-(3-(3-hydroxyphenyl)-3-oxopropyl)-2-methoxyphenyl) phosphate showing one spot on TLC.

In a similar manner there are obtained 2.1 sodium bis(3-(3-(2-hydroxyphenyl)-3-oxopropyl)-phenyl) phosphate
2.2 sodium bis(3-(3-(2,4-dihydroxyphenyl)-3-oxopropyl)phenyl) phosphate
2.5 sodium bis(4-(4-(2,4-dihydroxyphenyl)-4-oxobutyl)phenyl) phosphate
2.4 sodium bis(3-(3-(2,4,6-trihydroxyphenyl)-3-oxopropyl)phenyl) phosphate
sodium bis(3-(3-(4-hydroxyphenyl-3-oxopropyl)phenyl) phosphate
sodium bis(3-(3-(4-hydroxy-3-methoxyphenyl)propionyl)phenyl) phosphate -hydroxyphenyl)-propiophenone -benzoyloxy-
Using hexaacetate starting from phosphorus oxychloride and 2'-benzoyloxy-3-(3-hydroxyphenyl)-propiophenone, 2', 4'- dibenzoyloxy-3-(3-hydroxphenyl)propiophenone, 2',-4'-dibenzoyloxy-4-(4-hydroxphenyl)-butyrophenone, 3-(3-hydroxyphenyl)-2',4',6'-tribenzoyloxy propiophenone, 4'-benzoyloxy-3(3-hydroxphenyl)-propiophenone and 4'-benzoyloxy- 3-(3-hydroxyphenyl)-3'-methoxypropiophenone respectively. Using the method described in example 10 there are obtained the diacetate of the compounds 2.1, the tetra acetates of the compounds 2.2 and 2.5 and the hexacetate of compound 2.4.

EXAMPLE 6

10.8 g of 2', 4'-dimethyl-3-(4-hydroxyphenyl)propiophenone is dissolved in 215 ml of dry pyridine, and this solution is slowly added (1 h) with stirring to a solution of 27 ml phosphorus oxychloride in 250 ml dry pyridine at −10°. After another hour at −10° and one hour at room temperature the reaction mixture is poured on crushed ice (500 g). Next day the solution obtained is evaporated in vacuo and the residue dissolved in a mixture of 200 ml of ethyl acetate and 200 ml 2.5 M hydrochloric acid. The organic phase is collected, and the aqueous phase is extracted once more with ethyl acetate. The combined organic phases are washed twice with water and then dried with magnesium sulfate. The solvent is removed in vacuo and 4-(3-(2,4-dimethylphenyl)-3-oxopropyl)phenyl dihydrogen phosphate is obtained as a yellow glass.

EXAMPLE 7

2.4 g of 4-(3-(2.4-dimethyl)phenyl)-3-oxopropyl)-phenyl dihydrogen phosphate obtained according to Example 6 is dissolved in dry pyridine (20 ml) and the pyridine then evaporated in vacuo. This drying process is repeated twice and the residue is then dissolved in dry pyridine (30 ml) and triethylamine (2.02 ml) and 1,3,5-triisopropylbenzenesulphonyl chloride (4.46 g) is added. The reaction mixture is kept at room temperature for 2 h and after addition of 2',4'-dimethyl-3-(4-hydroxyphenyl)propiophenone (1.76 g) left for 70 h at the same temperature. Water is then added and the resulting solution poured in an excess of 2M hydrochloric acid. The resulting precipitate is collected by filtration, washed with water and then dissolved in ethanol-water with sodium hydroxide to a pH-value of about 5. An amount of 0.4 M acetic buffer (pH 5) corresponding to about half the volume of the reaction mixture is added, and the resulting mixture is boiled for 15 hrs so that all unreacted monophosphate ester is hydrolyzed. The unphosphorylated product is removed by extraction with ether and pure (TLC) bis(4-(3-(2,4-dimethylphenyl)-3-oxopropyl)phenyl) hydrogen phosphate is obtained by precipitation with hydrochloric acid and washing the precipitate with water.

EXAMPLE 8

To a mixture of 30.3 g of bis(4-(3-(3-hydroxyphenyl)-3-oxopropyl)-2-methoxyphenyl) hydrogen phosphate and 1000 ml of 0.3 M sodium ethoxide kept under nitrogen, 9.45 g of chloroacetic acid in 50 ml anhydrous ethanol is added dropwise with stirring and the mixture being kept boiling. After all of the acid is added the refluxing is continued for one hour. The reaction mixture is cooled and sodium chloride is removed by filtration. The solvent is evaporated under vacuum, and the residue is dissolved in water, acidified with 2 M hydrochloric acid and extracted with ethyl acetate. The organic layer is washed with saturated sodium sulfate solution. Water is added and pH adjusted to 7 with 2 M sodium hydroxide. The water layer is freeze-dried giving trisodium bis(4-(3-(3-(carboxylatomethoxy)phenyl)-3-oxopropyl)-phenyl) phosphate.

EXAMPLE 9

2.8 ml triethylamine in 10 ml of dry benzene is added dropwise during 40 min to a refluxing solution of 6.5 g 3-(4-diethylaminophenyl)-3',5'-dimethyl-4'-hydroxypropiophenone in 50 ml of dry benzene and 0.915 ml of $POCl_3$. Heating is continued for a further hour. The cooled, filtered solution is evaporated in vacuo, water is added and the pH is adjusted to 9. The mixture is evaporated to dryness in vacuo, acetone is added and undissolved sodium chloride and some disodium monophosphate is filtered. Light petroleum is added cautiously to separate disodium monoester, monosodium diester and triester from each other. The diester fraction is dissolved in acetone and a new fractionated precipitation with light petroleum is done. TLC (propan-2-ol : 0.5 M triethylamine bicarbonate, 8:2) of the precipitate, sodium bis(4-(3-(4-diethylaminophenyl)-propionyl)-2,6-dimethylphenyl) phosphate, shows one spot.

In a similar manner there are obtained sodium bis(3-(3-(4-diethylaminophenyl)propionyl)-phenyl) phosphate
sodium bis(3-(3-(3-dimethylaminomethyl-4-methoxyphenyl)propionyl)phenyl) phosphate
sodium bis(4-(3-(4-diethylaminophenyl))-2-(4-methylphenyl)acryloyl)-3-methoxyphenyl) phosphate starting from phosphorus oxychloride and 3-(4-diethylaminophenyl)-3'-hydroxypropiophenone,
3-(3-dimethylaminomethyl-4-methoxyphenyl)-3'-hydroxypropiophenone and
3-(4-diethylaminophenyl)-4'-hydroxy-2'-methoxy-2(4-methylphenyl)-acrylophenone respectively.

EXAMPLE 10

Acetic anhydride (5.1 g, 50 mmoles) is added to a solution of sodium bis(4-(3-oxo-3-(2,4,6-trihydroxyphenyl)propyl)phenyl) phosphate (3.16 g, 5 mmoles) in 20 ml of pyridine and triethylamine (1.02 g, 10 mmol). The mixture is kept at room temperature for 18 hours and poured on 200 g of ice-water. The pH of the mixture is adjusted to 1 with 1 M hydrochloric acid at 0°. The aqueous phase is discarded. The residue is ground with ice-water and dissolved in acetone : aq., 1:3. The pH of the solution is adjusted to 4.0. The acetone is evaporated in vacuo and the remaining syrup precipitate which solidifies on standing is almost pure 1.4 sodium bis(4-(3-oxo-3-(2,4,6-triacetoxyphenyl)-propyl)-phenyl) phosphate according to analysis of the content of acetoxy groups.

In a similar manner the following compounds are obtained 1.5 sodium bis(4-(3-oxo-3-(2,4,6-tripropionyloxyphenyl)propyl)phenyl) phosphate
1.18 sodium bis(4-(3-(3-acetoxyphenyl)-3-oxopropyl)-2-methoxyphenyl) phosphate
1.19 sodium bis(4-(3-oxo-3-(3-propionyloxyphenyl)-propyl)-2-methoxyphenyl) phosphate 1.35 sodium bis(4-(3-(4-acetamidophenyl)-3-oxopropyl)-2-methoxyphenyl) phosphate
1.33 sodium bis(4-(3-(2-acetamidophenyl-3-oxopropyl)-2-methoxyphenyl) phosphate
1.34 sodium bis(2-methoxy-4-(3-oxo-3-(3-propionamidophenyl)propyl)-phenyl) phosphate
1.39 sodium bis(3-acetoxy-4-(3-phenylpropionyl)phenyl) phosphate
1.40 sodium bis(4-(3-phenylpropionyl)-3-propionyloxyphenyl) phosphate
1.43 sodium bis(3-acetoxy-4-(3-(4-chlorophenyl)propionylphenyl) phosphate
1.44 sodium bis(4-(3-(4-chlorophenyl)propionyl)-3-propionyloxyphenyl) phosphate
1.41 sodium bis(3-acetoxy-4-(3-(4-methoxyphenyl)propionyl) phenyl) phosphate
1.42 sodium bis(4-(3-(4-methoxyphenyl)propionyl)-3-propionyloxyphenyl) phosphate
1.62 sodium bis(4-(3-(4-acetamidophenyl)propionyl)-3-methoxyphenyl) phosphate
1.73 sodium bis(4-(3-(4-acetoxy-3,5-dimethoxyphenyl)propionyl) phenyl) phosphate
1.74 sodium bis(3-(3-(4-acetoxy-3,5-dimethoxyphenyl)propienyl) phenyl)
2.8 sodium bis(3-(3-(2-acetamidophenyl)-3-oxopropyl)phenyl) phosphate The starting material for compounds 1.4 and 1.5 are found in example 12, for compounds 1.18 and 1.19 in example 5, and for compounds 1.33, 1.34, 1.35, 1.62, and 2.8 in example 3.

Compounds 1.39 and 1.40 are prepared from sodium bis (3-hydroxy-4-(3-phenylpropionyl) phenyl) phosphate (prepared according to example 5).

Compounds 1.41 and 1.42 are prepared from sodium bis (3-hydroxy-4-(3-(4-methoxyphenyl) propionyl) phenyl) phosphate (prepared according to example 5).

Compounds 1.43 and 1.44 are prepared from sodium bis (4-(3-(4-chlorophenyl)propionyl)-3-hydroxy phenyl) phosphate (prepared according to example 5).

Compound 1.73 is prepared from sodium bis (4-(3-(3,5-dimethoxy-4-hydroxy-phenyl) propionyl) phenyl) phosphate (obtained by partial demethylation of its dimethyl ether, which is prepared according to example 1).

Compound 1.74 is prepared from sodium bis (3-(3-(3,5-dimethoxy-4-hydroxy-phenyl) propionyl) phenyl) phosphate (obtained by partial demethylation of its dimethyl ether, which is prepared according to example 1).

EXAMPLE 11

2',4',6'-tribenzoyloxyacetophenone (83.5 g) and 4-hydroxybenzaldehyde are dissolved in 850 ml of ethyl acetate. Hydrogen chloride is led in at a temperature of 0° for 6 h. The reaction mixture is then kept at about 5° for 4 days and then freed from most of the hydrogen chloride with nitrogen passed through the solution. The ethyl acetate is evaporated and the residue mixed with 300 ml benzene and evaporated to remove the remaining hydrogen chloride. The residue is mixed with abs. ethanol (460 ml). A crystalline solid is formed, collected by filtration and then suspended in ether and refluxed with stirring for 2 h. After cooling, filtration and washing with ether there is obtained 41 g of 4-hydroxy-2',4',6'-tribenzoyloxy-chalcone with m.p. 198°–200°. This compound is dissolved in 1400 ml dioxane and hydrogenated at room temperature and atmospheric pressure with 4 g of 10 % Pd/C C as catalyst. When the theoretical amount of hydrogen has been absorbed the reaction is stopped, the catalyst removed by filtration and the dioxane evaporated in vacuo. The residue is recrystallized twice from abs. ethanol and 28 g of 3-(4-hydroxyphenyl)-2',4',6'-tribenzoyloxypropiophenone is obtained with a m.p. of 156°–8°.

EXAMPLE 12

A solution of 3-(4-hydroxyphenyl)-2',4',6'-tribenzoyloxypropiophenone (60 g) in 120 ml of anhydrous pyridine is added over two hours to a solution of phosphorus oxychloride (4.6 ml) in 50 ml of pyridine at −20° C. The mixture is kept for 2 hours at −5°, for 60 hours at room temperature, for 1 hour at 70°–80° and then cooled to room temperature. Water is added until the solution becomes opalescent. The mixture is stirred over night and then added to a mixture of 1000 ml of 2.5 M hydrochloric acid and about 400 ml of ethyl acetate. The organic phase is washed with water and a saturated sodium sulfate solution and dried with sodium sulfate. The solvent is evaporated and the residue is chromatographed on silica gel. The fraction containing bis(4-(3-oxo-3-(2,4,6-tribenzoyloxyphenyl)-propyl)phenyl)hydrogen phosphate, as checked with TLC, is collected and the solvent evaporated. The residue is dissolved in acetone and 80 ml of 2 M sodium hydroxide in 210 ml of methanol is added. After 10 min pH is adjusted to 3 with hydrochloric acid. Water is added until the solution becomes opalescent and the mixture is steam distilled. The residue is decanted, cooled to 0° and filtered. The collected solid is mixed with ethyl acetate and 0.2 M hydrochloric acid. The organic phase is washed with a saturated sodium sulfate solution. The residue after evaporation is dissolved in acetone : water, and pH is adjusted to 4 with sodium hydroxide. The acetone is evaporated and the remaining solution freeze-dried, giving sodium bis(4-(3-oxo-3-(2,4,6-trihydroxyphenyl)-propyl)phenyl) phosphate, showing one spot on TLC.

In a similar manner 2.3 sodium bis(5-(3-(2,6-dihydroxyphenyl)-3-oxopropyl)-2-methoxyphenyl)phosphate is obtained starting from phosphorus oxychloride and 2',6'-dibenzoyloxy 3-(3-hydroxy-4-methoxyphenyl)-propiophenone.

The tetra acetate of the above mentioned compound, (2.3) is obtained according to the method described in example 10.

EXAMPLE 13

3-(4-methoxyphenyl)-2',6'-dimethoxy-4'-hydroxy-propiophenone (6 g) and N-methylphosphoramidic dichloride (1.41 g) are dissolved in dry benzene (20 ml). The solution is refluxed, and triethylamine (1.92 g) dissolved in dry benzene (10 ml) is added dropwise with stirring. The reaction mixture is refluxed for 3 h. The benzene solution is cooled, washed with 0.5 M hydrochloric acid, water and 0.5 M sodium bicarbonate. The organic phase is dried with magnesium sulfate, filtered and evaporated to dryness. The residue is dissolved in 200 ml of a mixture of 1 part 1 M sulfuric acid and 3 parts of acetone and refluxed for 4 h. The acetone is evaporated under vacuum, and the aqueous residue extracted with ethylacetate. The organic phase is washed with water and dried and then evaporated under vacuum. The residue is dissolved in methanol and pH is adjusted to 7 with 2 M sodium hydroxide. The methanol is evaporated under vacuum and the substance left is dissolved in acetone and precipitated with ether. The precipitate (4 g) is:

sodium bis(3,5-dimethoxy-4-(3-(4-methoxyphenyl)-propionyl)phenyl) phosphate showing one spot in TLC (silica gel, n-butanol - water).

In a similar manner the following compounds are obtained starting from N-methylphosphoramidic dichloride and a corresponding monophenolic compound being a substituted chalcone or dihydrochalcone with the free phenolic hydroxy group situated in one of the two benzene rings of the chalcone — or dihydrochalcone skeleton and always in a position not ortho to the carbon-chain between these two benzene rings. The different substituted chalcones and dihydrochalcones, which are used as starting material together with N-methylphosphoramidic dichloride will be clearly understood from the names of the endproducts mentioned below.

sodium bis(4-(3-oxo-3-(2,4,6-trimethoxyphenyl)-propyl)phenyl phosphate
sodium bis(3-methoxy-4-(3-phenylpropionyl)phenyl phosphate
sodium bis(3-methoxy-4-(2-methyl-3-phenylpropionyl)phenyl) phosphate
sodium bis(3-methoxy-4-(3-(2-methoxyphenyl)propionyl)phenyl) phosphate
sodium bis(4-(3-(2,4-dimethoxyphenyl)propionyl)-3-methoxyphenyl)phosphate
sodium bis(4-(3-(3,5-dimethoxyphenyl)propionyl)-3-methoxyphenyl) phosphate
sodium bis(3-methoxy-4-(3-(4-methylphenyl)propionyl)phenyl phosphate
sodium bis(4-(3-(2,4-dimethylphenyl)propionyl)-3-methoxyphenyl) phosphate
sodium bis(4-(3-(4-chlorophenyl)propionyl)-3-methoxyphenyl) phosphate
sodium bis(4-(3-(3-chlorophenyl)propionyl)-3-methoxyphenyl) phosphate
sodium bis(4-(3-(2-chlorophenyl)propionyl)-3-methoxyphenyl) phosphate
sodium bis(4-(3-(2,6-dichlorophenyl)propionyl)-3-methoxyphenyl) phosphate
sodium bis(4-(3-(2,4-dichlorophenyl)propionyl)-3-methoxyphenyl) phosphate
sodium bis(4-(3-(4-fluorophenyl)propionyl)-3-methoxyphenyl) phosphate
sodium bis(3-methoxy-4-(3-(4-nitrophenyl)-acryloyl)phenyl) phosphate
sodium bis(3,5-dimethoxy-4-(3-phenylpropionyl)phenyl) phosphate
sodium bis(3,5-dimethoxy-4-(3-(4-methylphenyl)propionyl)phenyl) phosphate
sodium bis(4-(3-(4-chlorophenyl)propionyl)-3,5-dimethoxyphenyl) phosphate
sodium bis(3-methyl-4-(3-phenylacryloyl)phenyl) phosphate
sodium bis(3-methyl-4-(3-phenylpropionyl)phenyl) phosphate
sodium bis(4-(3-(4-chlorophenyl)propionyl)-3-methylphenyl) phosphate
sodium bis(4-(3-(3,5-dimethoxyphenyl)propionyl)-3-methylphenyl) phosphate
sodium bis(4-(3-(4-methoxyphenyl)-2-methylpropionyl)-3-methylphenyl) phosphate
sodium bis(4-(3-(2,4-dimethoxyphenyl)-3-oxopropyl)-3-methylphenyl) phosphate
sodium bis(3-(3-(2-nitrophenyl)-3-oxopropenyl)phenyl) phosphate
sodium bis(3-(3-(4-methylphenyl)-3-oxopropyl)phenyl) phosphate
sodium bis(3-(3-(4-chlorophenyl)acryloyl)phenyl) phosphate
sodium bis(3-(3-(4-chlorophenyl)propionyl)phenyl) phosphate
sodium bis(3-(3-(3-methoxyphenyl)-2-methylpropionyl)phenyl) phosphate
sodium bis(3-(3-(4-isopropylphenyl)propionyl)phenyl) phosphate
sodium bis(4-(2,3-diphenylacryloxyl)-3-methoxyphenyl) phosphate

EXAMPLE 14

A solution of triethylamine (2.62 ml) in benzene (10 ml) is slowly added (20 min.) to a refluxing solution of N-methylphosphoramidic dichloride (1.37 g) and 2'-hydroxy-3-(4-hydroxyphenyl)-propiophenone (4.5 g) in dry benzene (40 ml). Heating is continued for another hour. After cooling the precipitated triethylamine hydrochloride is removed by filtration and the benzene solution washed with dilute hydrochloric acid, sodium hydrogen carbonate solution and water. After drying of the solution over anhydrous sodium sulfate the benzene is removed by evaporation in vacuo. The diester amidate obtained is heated under reflux in 50 % aqueous formic acid for 1 h. The solvents are evaporated in vacuo. Methanol is added and the undissolved material is filtered off. The pH of the solution is adjusted to 7 with 5 M sodium hydroxide, the methanol evaporated and the residue dissolved in acetone and precipitated with ether. The precipitate is sodium bis(4-(3-(2-hydroxyphenyl)-3-oxopropyl)phenyl)-phosphate showing one spot in TLC.

In a similar manner the following compound is obtained.

Sodium bis(4-(3-(2,4-dihydroxyphenyl)-3-oxopropyl)-phenyl) phosphate from 2'-hydroxy-3-(4-hydroxyphenyl)-4'-(methoxymethoxy)propiophenone.

EXAMPLE 15

12.6 g of the 4',5-dibenzoate of naringenine (m.p. 212°–4°, prepared by partial debenzoylation of the naringenine-4',5,7-tribenzoate according to a method described by L. Farkas et al. in Chem. Ber. 102 (1969) 2583) is dissolved in 75 ml dry pyridine and slowly added (60 min) with stirring to a solution of 1.2 ml phosphorus oxychloride in 85 ml dry pyridine at −10°. After another hour at −10° the reaction mixture is kept at room temperature to the next day. It is then poured on crushed ice (85 g) and the remaining solution evaporated in vacuo to a volume of about 50 ml. This solution is poured into a mixture of 5 M hydrochloric acid (250 ml) and crushed ice (100 g). The precipitate obtained is collected by filtration, washed with water and then dried in vacuo. the dried precipitate is the bis(7-naringenine-4',5-dibenzoate) hydrogen phosphate. This compound, after debenzoylation with alkali in aqueous methanol (according to Example 1) is transformed by alkali to the corresponding chalcone-derivative with the structure shown below. It is isolated as a red-yellowish powder by freeze-drying a water solution of its sodium salt and is pure in TLC.

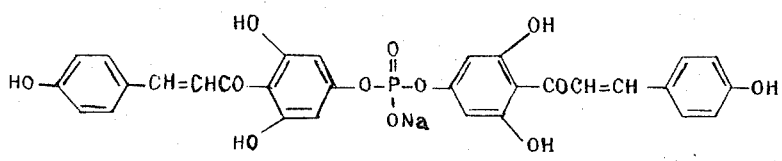

This chalcone phosphate is then hydrogenated with 10 % Pd/C in aqueous alkali to the corresponding dihydrochalcone, i.e. sodium bis(3,5-dihydroxy-4-(3-(4-hydroxyphenyl)propionyl)phenyl phosphate. This hydrogenated compound is also obtained directly from the bis(7-naringenine-4',5-dibenzoate) phosphate by hydrogenating this compound (2.2 g) dissolved in a mixture of dioxane (50 ml), ethanol (30 ml) and 0.65 M sodium hydroxide (80 ml) with 0.5 g 10 % Pd/C as catalyst.

Using the latter method the following compounds are obtained by hydrogenation of the corresponding substituted bis flavanone phosphate esters prepared from phosphorus oxychloride and substituted 4'-hydroxyflavanones. The substituents in question will be clearly understood from the endproducts mentioned below.

sodium bis(4-(3-(2-hydroxyphenyl)-3-oxopropyl)-3-methylphenyl) phosphate
sodium bis(2,5-dimethyl-4-(3-(2-hydroxyphenyl)-3-oxopropyl)-phenyl) phosphate
sodium bis(3-ethyl-4-(3-(2-hydroxyphenyl)-3-oxopropyl)-2-methoxyphenyl) phosphate
sodium bis(4-(3-(2-hydroxy-5-methylphenyl)-3-oxopropyl)-3-methylphenyl) phosphate
sodium bis(4-(3-(2-hydroxy-4-methoxyphenyl)-3-oxopropyl)-3-methylphenyl) phosphate
sodium bis(2,3-dimethyl-4-(3-(2-hydroxylphenyl)-3-oxopropyl)phenyl phosphate
sodium bis(4-(3-(4-chloro-2-hydroxyphenyl)-3-oxopropyl)-3-methylphenyl) phosphate
-propionylphenyl) phosphate is obtained according to the method described in Example 10.

EXAMPLE 16

3-(4-hydroxyphenyl)-2',4',6'-trimethoxypropiophenone (2.08 g, 6.6 mmoles), tetrahydrofuran (6 ml), pyridine (0.54 ml, 6.7 mmoles) and 2-chloromethyl-4-nitrophenyl phosphorodichloridate (0.91 g, 3 mmoles) are kept for 24 h at room temperature, and then 1 h at 60°. After cooling pyridine hydrochloride is filtered off and the solvent is evaporated. The residue is dissolved in benzene and chromatographed on a silica gel column. The tertiary phosphate ester is eluated with benzene and evaporated. Yield 1.05 g.

0.864 g of the tertiary phosphate is dissolved in 10 ml of pyridine. Water is added until the solution becomes opalescent. The solution is kept at room temperature for 2 days and then heated at 80° for 8 h. The reaction is followed on TLC (water - n - BuOH). The reaction mixture is poured into 20 ml of ethylacetate and 0.2 M hydrochloric acid. The filtered ethylacetate solution is evaporated in vacuo. Methanol is added and the undissolved is filtered off. The pH of the solution is adjusted to 7 with 5 M sodium hydroxide, evaporated, dissolved in acetone and precipitated with ether. Yield 0.31 g of sodium bis(4-(3-oxo-3-(2,4,6-trimethoxyphenyl)-propyl)phenyl) phosphate.

EXAMPLE 17

This example illustrates the smooth muscle stimulatory effect of esters of this invention on the gerbil colon in vivo.

The experiments are performed with mongolian gerbils, anesthetized with pentobarbital, 50 mg/kg. The ascending colon is exposed and carefully stretched between silk thread loops and a strain-gauge transducer.

After a stable base-line has been established an ester of this invention, sodium bis (4-(3-oxo-3-(2,4,6-trihydroxyphenyl)-propyl)phenyl) phosphate is infused i.v.

In doses from 40 mg/kg this treatment causes the gut to respond with a series of contractions.

Sodium bis(3,5-dihydroxy-4(3-(4-hydroxyphenyl)-propionyl)phenyl) phosphate and sodium bis(4-(3-(2,4-dihydroxyphenyl)-3-oxopropyl)phenyl) phosphate also give contraction in the same dose range while sodium diphenyl phosphates causes no effects at all in doses up to 400 mg/kg.

EXAMPLE 18

Sodium bis(3-(3-(4-hydroxyphenyl)-3-oxopropyl)-phenyl phosphate (2 g) (see example 5) is dissolved in dry pyridine (35 ml). This solution is added with stirring during 15 minutes to a solution of phosphorus oxychloride (1.6 ml, 0.018 mole) in dry pyridine (50 ml) at −10° C. The resulting reaction mixture is kept at −10° C for an additional hour. The temperature is then allowed to rise to room temperature.

The next day the clear solution is poured on crushed ice (50 g) and most of the pyridine is removed under vacuum. To the residue 5 M sodium hydroxide solution (18 ml) is added to get pH of about 8.5, and the solution obtained is extracted several times with ether.

The water solution is then poured in cold 5 M hydrochloric acid, (50 ml) and the resulting precipitate, collected by filtration, washed with water and dried under vacuum, is the bis(dihydrogen phosphate) of bis(3-(3-(4-hydroxyphenyl)-3-oxopropyl)phenyl hydrogen phosphate.

EXAMPLE 19

The PG-inhibitory effect of esters of the present invention on the gerbil colon are determined using the general technique described by Eakins, Miller & Karim (J. Pharm. Exp. Ther. 176:441, 1971). Gerbils (*Meriones unguiculatus*) of own breed, both sexes, weighing 50–80 g are used. The animal is stunned, colon ascendens immediately removed, and a 2–3 cm piece mounted in a 6 ml bath containing a modified de Jalon solution at 28° C and continuously oxygenated. Contractions of the organ are registered either isotonically or isometrically. When testing the inhibitory effect of a compound this is added to the bath 2 min before the addition of prostaglandin. The antagonist (esters of this invention) is usually dissolved in saline, but occasionally an organic solvent such as ethanol has to be included. Several concentrations of each antagonist are used. In this system prostaglandins $E_1$, $E_2$ $F_{1\alpha}$ and $F_{2\alpha}$ produce suitable contractions of the organ in the concentration range 1–40 mg/ml.

Results from these experiments give an approximate idea of the PG-inhibitory potency of the compounds. When more precise information about this is desired we use a more elaborate method involving the establishment of several PG dose-response curves in the presence of various concentrations of inhibitor. The method used is essentially the same as that described by Arunlakshana & Schild (Br. J. Pharm. 14:48, 1959). Other agonists, acetylcholine,5-HT and bradykinin, are included in these experiments in order to determine the selectivity of the antagonism.

Esters of the present invention cause a dose-dependent inhibition of the responses of the gut preparation to either of the prostaglandins tested. The concentration of polyphloretin phosphate (PPP) required to produce a 50 per cent reduction of the PG-induced contraction is 10–75 µg/ml, the antagonist-agonist ratio being in the order of 2000–4000. The corresponding concentration of sodium bis(4-(3-oxo-3-(2,4,6-trihydroxyphenyl)-propyl)phenyl)phosphate is only about one tenth and of sodium bis(3,5-dihydroxy-4-(3-(4-hydroxyphenyl)propionyl)phenyl)phosphate one fourth of that of PPP. The sodium salt of diphenylphosphate is without effect in concentrations 10 times as high as that of PPP.

In the quantitative assay it is confirmed that sodium bis(4-(3-oxo-3-(2,4,6-trihydroxyphenyl)propyl)-phenyl)phosphate has a PG inhibition potency about 10 times that of PPP on a weight basis, and also the results with sodium bis (3,5-dihydroxy-4-(3-(4-hydroxyphenyl)propionyl)phenyl)phosphate are confirmed. In addition on the results with other agonists than prostaglandins show that the antagonism is very selective, far higher concentrations than the prostaglandin-inhibitory ones having no influence on the contractions elicited by acetylcholine, 5-HT or bradykinin.

The selective inhibitory effects of the following compounds are found to be equal to or superior to that of PPP.

sodium bis(4-(3-(2-hydroxyphenyl)-3-oxopropyl)-phenyl)phosphate
sodium bis(4-(3-(2,4-dihydroxyphenyl)-3-oxopropyl)-phenyl) phosphate
sodium bis(4-(3-(2-hydroxyphenyl)-3-oxopropyl)-3-methylphenyl) phosphate
trisodium bis(4-(3-(3-(carboxylatomethoxy)phenyl)-3-oxopropyl)-phenyl) phosphate
sodium bis(4-(3-(2-aminophenyl)-3-oxopropyl)phenyl) phosphate
sodium bis(4-(3-(3-aminophenyl)-3-oxopropyl)phenyl) phosphate
sodium bis(4-(3-(4-aminophenyl)-3-oxopropyl)phenyl) phosphate
sodium bis(4-(3-(4-aminophenyl)propionyl)-3-methoxyphenyl) phosphate
sodium bis(3-(3-(2-aminophenyl)-3-oxopropyl)phenyl) phosphate
sodium bis(3-(3-(2,6-dihydroxyphenyl)-3-oxopropyl)-2-methoxyphenyl) phosphate
sodium bis(3-(3-(2-hydroxyphenyl)-3-oxopropyl)phenyl) phosphate
sodium bis(3-(3-(2,4-dihydroxyphenyl)-3-oxopropyl)-phenyl) phosphate
sodium bis(4-(4-(2,4-dihydroxyphenyl)-4-oxobutyl)-phenyl) phosphate
sodium bis(3-(3-(2,4,6-trihydroxyphenyl)-3-oxopropyl)phenyl phosphate
sodium bis(3-(3-(4-hydroxyphenyl)-3-oxopropyl)phenyl) phosphate
sodium bis(3-(3-(4-diethylaminophenyl)propionyl)-phenyl) phosphate
sodium bis(3-(3-(3-dimethylaminomethyl-4-methoxyphenyl)propionyl) phenyl) phosphate
sodium bis(4-(3-(4-diethylaminophenyl)-2-(4-methylphenyl) acryloyl)-3-methoxyphenyl) phosphate
sodium bis(4-(3-(4-diethylaminophenyl)propionyl)-2,6-dimethyl phenyl) phosphate
trisodium bis(3-(3-(4-carboxylatophenyl)propionyl)-phenyl) phosphate
sodium bis(3-(3-(4-hydroxy-3-methoxyphenyl)propionyl)phenyl) phosphate
trisodium bis(4-(3-(4-carboxylatophenyl)-2-(4-methyl-phenyl)-acryloyl)-3-methoxyphenyl) phosphate
trisodium bis(3-(3-(4-carboxylatomethylphenyl)-3-oxopropyl)phenyl) phosphate
sodium bis(3-(3-(4-methoxycarbonylmethylphenyl)-3-oxo-propyl) phenyl) phosphate
sodium bis(3-(3-(4-(N,N-dimethylcarbamoylmethyl)-phenyl)-3-oxopropyl)phenyl) phosphate
bis(dihydrogenphosphate) of bis(3-(3-(4-hydroxyphenyl)-3-oxopropyl) phenyl)hydrogen phosphate

EXAMPLE 20

Effects of esters of the present invention are also studied on a rat uterus preparation, using an established technique (Staff of the Department of Pharmacology, University of Edinburgh: Pharmacological Experiments on Isolated Preparations, E & S Livingstone Ltd, Edinburgh and London 1968). In these experiments uterine horns from diethylstilbestrol-treated rats are suspended in a 6 ml bath containing modified de Jalon solution, kept at 28° C and gassed with air. When sodium bis(4-(3-oxo-3-(2,4,6-trihydroxyphenyl)-propyl)phenyl) phosphate is added in the concentration range 2–10 µg/ml a contraction is obtained demonstrating the smooth muscle stimulatory action of this compound.

Similar effects are also obtained with the following compounds:

sodium bis(4-(3-(2,4-dihydroxyphenyl)-3-oxopropyl)-phenyl) phosphate
trisodium bis(4-(3-(3-(carboxylatomethoxy)phenyl)-3-oxopropyl)-phenyl) phosphate.
sodium bis(3,5-dihydroxy-4-(3-(4-hydroxyphenyl)-acryloyl)phenyl) phosphate
sodium bis(3,5-dihydroxy-4-(3-(4-hydroxyphenyl)propionyl)phenyl) phosphate
sodium bis(3-(3-(2,4-dihydroxyphenyl)-3-oxopropyl)-phenyl) phosphate
sodium bis(5-(3-(2,6-dihydroxyphenyl)-3-oxopropyl)-2-methoxyphenyl) phosphate
sodium bis(3-(3-(2,4,6-trihydroxyphenyl)-3-oxopropyl)phenyl phosphate
sodium bis(4-(4-(2,4-dihydroxyphenyl)-4-oxobutyl)-phenyl) phosphate
sodium bis(3-(3-(4-hydroxyphenyl)-3-oxopropyl)phenyl) phosphate
bis(dihydrogenphosphate) of bis(3-(3-(4-hydroxyphenyl)-3-oxo-propyl)phenyl hydrogen phosphate trisodium bis(3-(3-(4-carboxylatomethylphenyl)-3-oxopropyl) phenyl) phosphate trisodium bis(3-(3-(4-carboxylatophenyl)propionyl)-phenyl) phosphate trisodium bis(4-(3-(4-carboxylatophenyl)-2-(4-methoxy-phenyl)-acryloyl)-3-methoxyphenyl) phosphate

EXAMPLE 21

The effects of esters of the present invention on bronchial smooth muscle have been investigated using an isolated perfused guinea-pig lung preparation according to Bhattacharya & Delaunois (Arch. Int. Pharmacodyn. 101:495, 1955). The lungs from guinea pigs weighing 300–400 g are removed, and the trachea and A. pulmonalis cannulated. The arterial cannula is connected to a perfusion fluid reservoir containing Tyrode solution buffered with 10 % Sorensen phosphate buffer. The tracheal cannula is connected with tubing to a carbogen gas supply delivering a constant amount per time unit. The perfusion pressure is measured in a side arm of the tubing with a "Mercury" transducer connected to an Ultralette UV-recorder. The compounds are injected via the arterial cannula, close to the entrance of A. pulmonalis in the lung. In this type of experiments sodium bis(4-(3-oxo-3-(2,4,6-trihydroxyphenyl)-propyl)phenyl) phosphate showed a bronchoconstricting effect when administered in a dose of about 0.5 mg and upwards.

The sodium salt of diphenyl phosphate completely lacked such an effect even when tested in the dose 12.8 mg.

Similar effects in a dose of about 0.5-2 mg are also obtained with the following compounds.

sodium bis(4-(3-(2,4-dihydroxyphenyl)-3-oxopropyl)-phenyl) phosphate trisodium bis(4-(3-(carboxylatometholxy)phenyl)-3-oxopropyl) phenyl) phosphate sodium bis(3,5-dihydroxy-4-(3-(4-hydroxyphenyl)-acryloyl)phenyl) phosphate sodium bis(3,5-(3,5-dihydroxy-4-(4-hydroxyphenyl)-propionyl)phenyl) phosphate sodium bis(3-(3-(2,4-dihydroxyphenyl)-3-oxopropyl)-phenyl)phosphate sodium bis(5-(3-(2,6-dihydroxyphenol)-3-oxopropyl)-2-methoxyphenyl) phosphate sodium bis(3-(3-(2,4,6-trihydroxyphenyl)-3-oxopropyl)phenyl phosphate sodium bis(4-(4-(2,4dihydroxyphenyl)-4-oxobutyl)-phenyl) phosphate soium bis(3-(3-(4-hydroxyphenyl)-3-oxopropyl)phenyl) phosphate bis(dihydrogenphosphate) of bis(3-(3-(4-hydroxyphenyl)-3-oxopropyl)phenyl hydrogen phosphate trisodium bis(3-(3-(4-carboxylatomethylphenyl)-3-oxopropyl) phenyl) phosphate trisodium bis(3-(3-(4-carboxylatophenyl)propionyl)-phenyl) phosphate trisodium bis(4-(3-(4-carboxylatophenyl)-2-(4-methoxy-phenyl)-acryloyl)-3-methoxyphenyl) phosphate

EXAMPLE 22

The antagonism to Slow Reacting Substance (SRS) is determined on the isolated guinea-pig ileum as described by Mathe & Strandberg (Acta physiol. scand. 82:460, 1971). Purified SRS is obtained from cat paws perfused with compound 48/80 (Strandberg & Uvnas: Acta physiol. scand. 82:358, 1971). Sodium bis(4-(3-oxo-3-(2,4,6-trihydroxyphenyl)propyl)phenyl) phosphate was tested in this system in several concentrations. In concentrations as low as 5 $\mu$g/ml, it inhibits contractions produced by SRS, but not by histamine and bradykinin, in a competitive manner, i.e. parallel shift of the dose-response curves and with no change in maximum contraction.

The sodium salt of diphenyl phosphate is found to be without effect.

The following compounds of this invention are also found to inhibit SRS.

sodium bis(4-(3-(2-hydroxyphenyl)-3-oxopropyl)-phenyl)phosphate sodium bis(4-(3-(2,4-dihydroxyphenyl)-3-oxopropyl)-phenyl)

sodium bis(4-(3-(2-hydroxyphenyl)-3-oxopropyl)-3methylphenyl) phosphate trisodium bis(4-(3-(3-carboxylatomethoxy)phenyl)-3-oxopropyl)-phenyl) phosphate sodium bis(3,5-dihydroxy-4-(3-(4-hydroxyphenyl)-acryloyl)phenyl) phosphate sodium bis(3,5-dihydroxy-4-(3-(4-hydroxyphenyl)propionyl)phenyl) phosphate sodium bis(5-(3-(2,6-dihydroxyphenyl)-3-oxopropyl)-2-methoxyphenyl) phosphate bis(dihydrogenphosphate) of bis(3-(3-(4-hydroxyphenyl)-3-oxopropyl) phenyl) hydrogen phosphate sodium bis(3-(3-(2-hydroxyphenyl)-3-oxopropyl)phenyl) phosphate sodium bis(3-(3-(2,4-dihydroxyphenyl)-3-oxopropyl)-phenyl) phosphate sodium bis(4-(4-(2,4-dihydroxyphenyl)-4-oxobutyl)-phenyl) phosphate sodium bis(3-(2,4,6-trihydroxyphenyl)-3-oxopropyl)-phenyl phosphate sodium bis(3-(3-(4-hydroxyphenyl)-3-oxopropyl)phenyl) phosphate trisodium bis(3-(3-(4-carboxylatomethylphenyl)-3-oxopropyl)phenyl) phosphate trisodium bis(3-(3-(4-carboxylatophenyl)propionyl)phenyl) phosphate sodium bis(3-(3-(4-hydroxy-3-methoxyphenyl)propionyl)phenyl) phosphate trisodium bis(4-(3-(4-carboxylatophenyl)-2-(4-methoxy-phenyl)-acryloyl)-3-methoxyphenyl) phosphate

EXAMPLE 23

| Manufacturing Process for tablets a 25 mg. Model batch of 1000 tablets. | |
|---|---|
| Sodium bis(4-(3-(2-hydroxyphenyl)-3-oxopropyl) phenyl)phosphate, mesh 70 | 25.0 g. |
| I Lactosum, Ph.Nord | 210 g. |
| Amylum maidis, Ph.Nord. | 75 g. |
| II Kollidon 25, B.A.S.F. | 3.5 g. |
| Aqua purificata q.s. | |
| III Talcum, Ph.Nord | 1.5 g. |
| Magnesii stearas, Ph. Nord. | 1.5 g. |

Weight of 1000 tablets: 330 g.
Weight of 1 tablet: 330 mg.

Punch: 10.5 mm round, flat, scored, bevel-edged.

Mix the screened substances I thoroughly and then moisten with II, whereupon it is granulated through a stainless sieve no. 10 (mesh 25). Dry the granulate in an oven at a maximum temperature of 40° C, then repeat sieving through sieve no. 10. Add the substances under III and mix thoroughly. Punch tablets with a gross weight of about 330 mg.

EXAMPLE 24

| Manufacturing Process for tablets a 25 mg. Model batch of 1000 tablets. | |
|---|---|
| I Sodium bis(4-(3-oxo-3-(2,4,6-trihydroxyphenyl)-propyl)phenyl)phosphate, mesh 70 | 25.0 g. |
| Avicel, FMC Corporation, USA | 76 g. |
| II Amylum maidis, Ph.Nord | 76 g. |
| Calcii phosphas, Ph.Nord | 76 g. |
| III Talcum, Ph.Nord | 15 g. |
| Magnesii stearas, Ph.Nord | 2 g. |
| Weight of 1000 tablets: 270 g. Weight of 1 tablet: 270 mg. | |

Punch: 9,0 mm round, normal concave.

Mix I by gradual stages with II. Add the substances under III and mix thoroughly. Punch tablets with a gross weight of about 270 mg.

EXAMPLE 25

| Oral suspension 5 mg/ml. | |
|---|---|
| Sodium bis(4-(3-(4-chlorophenyl)propionyl)-3,5-dimethoxyphenyl) phosphate | 5 mg. |
| Sorbitol | 600 mg. |
| Ascorbic acid | 100 mg. |
| Flavouring compound | q.s. |
| Colour | q.s. |
| Water to make | 1 ml. |

EXAMPLE 26

| Vagitoria 25 mg. | |
|---|---|
| Sodium bis(4-(3-oxo-3-(2,4,6-trihydroxyphenyl)-propyl)phenyl) phosphate | 25 mg. |
| Cacao butter | q.s. |

EXAMPLE 27

| Ointment 2% | |
|---|---|
| Sodium bis(3-(3-(2,4-dihydroxyphenyl)-3-oxopropyl)-phenyl) phosphate | 2 g. |
| Triethanolamine | 1 g. |
| Glycerol | 7 g. |
| Cetanol | 2.5 g. |
| Lanoline | 2.5 g. |
| Stearic acid | 20 g. |
| Sorbitan monooleate | 0.5 g. |
| Sodium hydroxide | 0.2 g. |
| Methyl paraben | 0.3 g. |
| Propyl paraben | 0.1 g. |
| Ethanol | 0.9 g. |
| Water to make | 100 g. |

EXAMPLE 28

| Eye-drops 2% | |
|---|---|
| Sodium bis(4-(3-(2,4-dihydroxyphenyl)-3-oxopropyl)phenyl) phosphate | 20 mg. |

| -continued | |
|---|---|
| Eye-drops 2% | |
| Boric acid | 10 mg. |
| Cetylpyridinium chloride | 25 μg. |
| Distilled water to make | 1 ml. |

EXAMPLE 29

| Aerosol for inhalation | |
|---|---|
| Sodium bis(4-(3-oxo-3-(2,4,6-trihydroxyphenyl)-propyl)phenyl)phosphate | 1 % |
| Isopropyl myristate | 1 % |
| Dichlorodifluoromethane | 39 % |
| Dichlorotetrafluoroethane | 59 % |
| Filled in a container with metered valve. Each dose gives 0,5 mg sodium bis(4-(3-oxo-3-(2,4,6-trihydroxyphenyl)propyl)phenyl) phosphate. | |

EXAMPLE 30

| Suspension for injection 20 mg/ml. | |
|---|---|
| Sodium bis(4-(3-(2,4-dimethoxyphenyl)propionyl)-3-methoxyphenyl) phosphate | 20 mg. |
| Sodium chloride | 8 mg. |
| Carboxy methylcellulose | 1 mg. |
| Benzyl alcohol | 1 mg. |
| Distilled water to make | 1 ml. |

EXAMPLE 31

| Injectable solution 20 mg/ml. | |
|---|---|
| Sodium bis(3-(3-(2,4,6-trihydroxyphenyl)-3-oxopropyl)phenyl)phosphate | 20 mg. |
| Ascorbic acid | 1 mg. |
| Sodium bisulfite | 1 mg. |
| Sodium chloride | 6 mg. |
| Methyl paraben | 0.7 mg. |
| Propyl paraben | 0.3 mg. |
| Distilled water to make | 1 ml. |

EXAMPLE 32

| Injectable solution 25 mg/ml. | |
|---|---|
| Sodium bis(4-(2-butyl-3-phenylpropionyl)phenyl) phosphate | 25 mg. |
| Benzyl alcohol | 50 mg. |
| Pea nut oil to make | 1 ml. |

EXAMPLE 33

| 40 mg Sterile powder to be dissolved in water for injection. | |
|---|---|
| Sodium bis(4-(3-oxo-3-(2,4,6-trihydroxyphenyl)propyl)-phenyl) phosphate | 40 mg. |
| Sodium chloride | 4 mg. |
| Methyl paraben | 0.7 mg. |
| Propyl paraben | 0.3 mg. |

The substances are dissolved in distilled water.
The solution is dispensed in vials and freeze-dried.

The above examples 23–33 to compositions are merely representative with regard to the active ingredients exemplified. It is to be understood that any other compounds disclosed in the foregoing examples 1–16 and 18 can well be substituted for the active ingredients illustrated in the above examples 23–33. Also, it is to be noted that two or more compounds of the invention may be used in combination in the compositions illustrated.

EXAMPLE 34

The action of esters of the present invention on the prostaglandin-stimulated glycolysis of the prepubertal ovary is investigated. The method used has been described in detail by Perklev & Ahren (Life Sciences Part I, 10:1387, 1971). In these experiments ovaries from prepubertal rats are removed and placed in Erlenmeyer flasks containing compounds of this invention dissolved in Krebs biocarbonate buffer. After that the ovaries have been preincubated during 60 min. at 37°C in this medium, they are blotted on filter paper and then washed for 2 min. in plain buffer. The ovaries are then transferred to a new incubation medium containing prostaglandins (PG) dissolved in Krebs bicarbonate buffer and incubated at 37°C for 2 hrs with continuous shaking. The ovarian glycolysis is then determined by measuring the concentration of lactic acid in the incubation medium. When polyphloretin phosphate (PPP) is present in the preincubation medium in a concentration of 500 μg/ml, the subsequent ovarian lactic acid production produced by $PGE_1$ is reduced to about 50% of that obtained with ovaries preincubated in plain buffer. When sodium bis(4-(3-(2,4,6-trihydroxyphenyl)propyl)phenyl)phosphate is investigated in the same experimental system, a 50% reduction of the lactate production is seen when only 50–100 μg/ml of the compound is present in the preincubation medium. Thus, this compound is 5–10 times more active as a prostaglandin inhibitor than PPP in the present experimental system. Prostaglandin inhibiting activity of the same order is also seen when the following compounds were tested:

sodium bis(4-(3-(2,4-dihydroxyphenyl)-3-oxopropyl)-phenyl)phosphate trisodium bis(4-(3-(3-(carboxylatomethoxy)phenyl)-3-oxopropyl)phenyl)phosphate sodium bis(3,5-dihydroxy-4-(3-(4-hydroxyphenyl)-acryloyl)phenyl)phosphate sodium bis(3,5-dihydroxy-4-(3-(4-hydroxyphenyl)-propionyl)phenyl)phosphate sodium bis(3-(3-(2,4-dihydroxyphenyl)-3-oxopropyl)-phenyl)phosphate sodium bis(5-(3-(2,6-dihydroxyphenyl)-3-oxopropyl)-2-methoxyphenyl)phosphate sodium bis(3-(3-(2,4,6-trihydroxyphenyl)-3-oxopropyl)phenyl phosphate sodium bis(4-(4-(2,4-dihydroxyphenyl)-4-oxobutyl)-phenyl)phosphate sodium bis(3-(3-(4-hydroxyphenyl)-3-oxopropyl)-phenyl)phosphate bis(dihydrogenphosphate) of bis(3-(3-(4-hydroxyphenyl)-3-oxopropyl)phenyl hydrogen phosphate trisodium bis(3-(3-(4-carboxylatomethylphenyl)-3-oxopropyl)phenyl)phosphate trisodium bis(3-(3-(4-carboxylatophenyl)propionyl)-phenyl)phosphate trisodium bis(4-(3-(4-carboxylatophenyl)-2-(4-methoxy-phenyl)acryloyl)-3-methoxyphenyl)phosphate Various modifications and equivalents will be apparent to one skilled in the art and may be made in the compounds, compositions and methods of the present invention without departing from the spirit or scope thereof, and it is therefore to be understood that the invention is to be limited only by the scope of the appended claims.

What we claim is:

1. A composition of matter suitable for use in counteracting the actions of an excessive formation and release of endogenous prostaglandins, unfavorable effects of exposure to exogenous prostaglandins, the actions of an excessive formation and release of slow reacting substance (SRS), and for producing a smooth muscle stimulatory effect, comprising as an active ingredient a compound according to Formula I in an amount effective for such purpose in combination with a pharmaceutically acceptable carrier, Formula I being:

(Claim 70, continued)

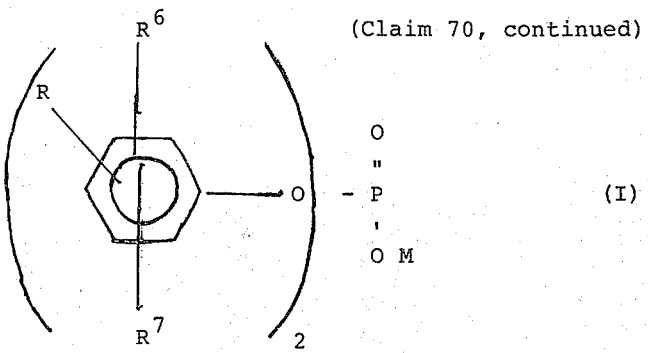

wherein R is positioned in m- or p-position relative to the phosphoric acid ester group and is

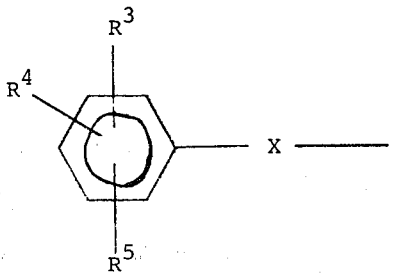

wherein X is selected from the group consisting of

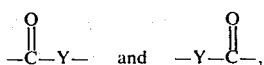

wherein Y is a straight hydrocarbon chain having 2 or 3 carbon atoms, said chain being saturated or containing one double bond and having at most 2 hydrogen atoms substituted by substituents selected from the group consisting of lower alkyl, lower alkenyl, phenyl, phenyl substituted in p-position by lower alkyl, lower alkoxy, halogen (F, Cl, Br) or $CF_3$, benzyl and benzyl substituted in p-position by lower alkyl, lower alkoxy, halogen (F, Cl, Br) or $CF_3$; $R^3$, $R^4$, $R^5$, $R^6$ and $R^7$ are the same or different and are selected from the group consisting of hydrogen, lower alkyl, lower alkenyl, lower alkoxy, hydroxy, hydroxy esterified with phosphoric acid, $OCOR^8$, F, Cl, Br, $CF_3$, $NO_2$, wherein $R^8$ is
  lower alkyl,
  where M is selected from the group consisting of H, Na, K, ½ Ca, and a pharmaceutically acceptable amine.

2. A composition according to claim 1, wherein at least two of substituents $R^3$, $R^4$, $R^5$, $R^6$ and $R^7$ are hydrogen 3. A composition according to claim 2, wherein Y contains one substituent selected from the group consisting of phenyl, phenyl substituted in p-positions, benzyl and benzyl substituted in p-position.

4. A composition according to claim 3, wherein Y is a straight substituted hydrocarbon chain having two carbon atoms.

5. A composition according to claim 4, wherein substituents $R^3$, $R^4$, $R^5$, $R^6$, $R^7$ are the same or different and are selected from the group consisting of hydrogen, lower alkyl, alkenyl, fluorine, chlorine, bromine, $CF_3$, hydroxy, hydroxy esterified with phosphoric acid, lower alkoxy, $OCOR^8$ and $NO_2$, wherein $R^8$ is lower alkyl.

6. A composition according to claim 2, wherein Y is a straight hydrocarbon chain having two or three carbon atoms, said chain being saturated or containing one double bond and having at most two hydrogen atoms substituted by substituents selected from the group consisting of lower alkyl and lower alkenyl.

7. A compound according to claim 6, wherein substituents $R^3$, $R^4$, $R^5$, $R^6$, $R^7$ are the same or different and are selected from the group consisting of hydrogen, lower alkyl, alkenyl, fluorine, chlorine, bromine, $CF_3$, hydroxy, hydroxy esterified with phosphoric acid, lower alkoxy, $OCOR^8$ and $NO_2$, wherein $R^8$ is lower alkyl.

8. A composition according to claim 7, wherein Y is a straight substituted or unsubstituted hydrocarbon chain having two carbon atoms.

9. A composition according to claim 7, wherein Y is a straight substituted or unsubstituted hydrocarbon chain having three carbon atoms.

10. A composition according to claim 9, wherein at least one of substituents $R^3$, $R^4$, $R^5$, $R^6$, $R^7$ is selected from the group consisting of hydroxy lower alkoxy, and $OCOR^8$, wherein $R^8$ is lower alkyl, said substituent being in o-position relative to the keto-group of X.

11. A composition according to claim 8, wherein at least one of substituents $R^3$, $R^4$, $R^5$, $R^6$, $R^7$ is selected from the group consisting of hydroxy, lower alkoxy, and $OCOR^8$, wherein $R^8$ is lower alkyl, said substituent being in o-position relative to the keto-group of X.

12. A composition according to claim 8, having substituents $R^3$, $R^4$, $R^5$, $R^6$ and $R^7$ which are selected from the group consisting of hydroxy, hydroxy esterified with phosphoric acid, lower alkoxy, $OCOR^8$ such substituents being positioned in m- and p-positions relative to the keto-group of X.

13. A composition according to claim 11, wherein X is

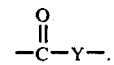

14. A composition according to claim 11, wherein X is

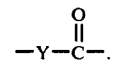

15. A composition according to claim 13, wherein R is positioned in p-position relative to the phosphoric acid ester group.

16. A composition according to claim 13, wherein R is positioned in m-position relative to the phosphoric acid ester group.

17. A composition according to claim 15, wherein Y is a straight unsubstituted hydrocarbon chain having two carbon atoms, said chain being saturated or containing one double bond.

18. A composition according to claim 15 and wherein Y is a straight hydrocarbon chain having two carbon atoms having at most two hydrogen atoms of the carbon atom adjacent to the keto-group substituted by substituents selected from the group containing lower alkyl and lower alkenyl.

19. A composition according to claim 1, wherein M is selected from the group consisting of Na, K, ½ Ca, diethanolamine, dimethylaminoethanol, N-methylglucamine, morpholine.

20. A composition according to claim 5, wherein the active ingredient is bis(3-(2,3-diphenyl-3-oxopropyl)-phenyl) hydrogen phosphate.

21. A composition according to claim 10, wherein the active ingredient is sodium bis(4-(4-(2,4-dihydroxyphenyl)-4-oxobutyl)phenyl phosphate.

22. A composition according to claim 12, wherein the active ingredient is sodium bis (4-(3-(3,5-dimethoxyphenyl)propionyl)-3-methylphenyl) phosphate.

23. A composition according to claim 12, wherein the active ingredient is bis (4-(2-butyl-3-phenylpropionyl)phenyl) hydrogen phosphate.

24. A composition according to claim 12, wherein the active ingredient is selected from the group consisting of sodium bis (3-(3-(4-hydroxyphenyl)-3-oxopropyl)phenyl) phosphate and its bis(dihydrogen phosphate)

25. A composition according to claim 12, wherein the active ingredient is sodium bis(3-(3-(3-methoxyphenyl)-2-methylpropionyl phenyl) phosphate.

26. A composition according to claim 12, wherein the active ingredient is sodium bis(3-(3-(4-hydroxy-3-methoxyphenyl)propionyl)phenyl phosphate.

27. A composition according to claim 14, wherein the active ingredient is sodium bis(3-acetoxy-4-(3-(4-methoxypheyl)propionyl)phenyl phosphate.

28. A composition according to claim 14, wherein the active ingredient is sodium bis(3,5-dihydroxy-4-(3-(4-hydroxyphenyl)acryloyl)phenyl) phosphate.

29. A composition according to claim 14, wherein the active ingredient is selected from the group consisting of sodium bis(3,5-dihydroxy-4-(3-(4-hydroxyphenyl)propionyl)phenyl) phosphate and its hexa acetate.

30. A composition according to claim 14, wherein the active ingredient is sodium bis(4-(3-(4-chlorophenyl)propionyl)-3-methoxyphenyl) phosphate.

31. A composition according to claim 14, wherein the active ingredient is sodium bis(3,5-dimethoxy-4-(3-(4-methylphenyl)propionyl)phenyl phosphate.

32. A composition according to claim 14, wherein the active ingredient is sodium bis(3-methoxy-4-(2-methyl-3-phenylpropionyl)phenyl) phosphate.

33. A composition according to claim 16 wherein the active ingredient is selected from the group consisting of sodium bis(3-(3-(2-hydroxyphenyl)-3-oxopropyl)phenyl) phosphate and its diacetate.

34. A composition according to claim 16 wherein the active ingredient is selected from the group consisting of sodium bis(3-(3-(2,4-dihydroxyphenyl)-3-oxopropyl)phenyl) phosphate and its tetra acetate.

35. A composition according to claim 16 wherein the active ingredient is selected from the group consisting of sodium bis(5-(3-(2,6-dihydroxyphenyl)-3-oxopropyl)-2-methoxyphenyl) phosphate and its tetra acetate.

36. A composition according to claim 16 wherein the active ingredient is selected from the group consisting of sodium bis(3-(3-(2,4,6-trihydroxyphenyl)-3-oxopropyl)phenyl) phosphate and its hexaacetate.

37. A composition according to claim 17, wherein the active ingredient is sodium bis(4-(3-(2-hydroxyphenyl)-3-oxopropyl)phenyl) phosphate.

38. A composition according to claim 17, wherein the active ingredient is

Sodium bis(4-(3-(2,4-dihydroxyphenyl)-3-oxopropyl)-phenyl) phosphate

39. A composition according to claim 17 wherein the active ingredient is selected from the group consisting of sodium bis(4-(3-oxo-3-(2,4,6-trihydroxyphenyl)-propyl)phenyl) phosphate and its hexa-acetate.

40. A composition according to claim 17, wherein the active ingredient is sodium bis(4-(3-(2-hydroxy-4-methoxyphenyl)-3-oxopropyl)-3-methylphenyl) phosphate.

41. A composition according to claim 17, wherein the active ingredient is sodium bis(4-(3-(4-chloro-2-hydroxyphenyl)-3-oxopropyl)-3-methylphenyl) phosphate.

42. A composition according to claim 17, wherein the active ingredient is sodium bis(4-(3-(2,4-dimethoxyphenyl)-3-oxopropyl)-3-methylphenyl) phosphate.

43. A method of treating an animal body suffering from the actions of an excessive formation and release of slow reacting substance (SRS) to counteract the unfavorable effects of such actions comprising administration of a therapeutically effective anti-SRS amount of a compound of Formula I to said animal body, as said Formula I is depicted in claim 1.

44. A method of treating an animal body to produce a smooth muscle stimulatory effect comprising administration of a smooth-muscle stimulatory amount of a compound of Formula I to said animal body, as said Formula I is depicted in claim 1.

45. A method of treating an animal body suffering from the actions of an excessive formation and release of endogenous prostaglandins to counteract the unfavorable effects of such actions comprising administration of a therapeutically effective amount of a compound of Formula I to said animal body, Formula I being:

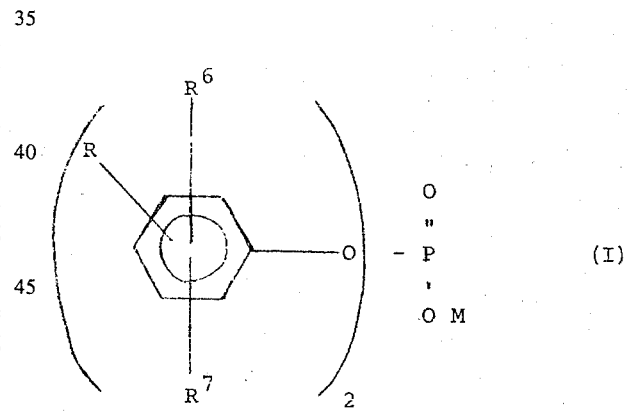

wherein R is positioned in m- or p-position relative to the phosphoric acid ester group and is

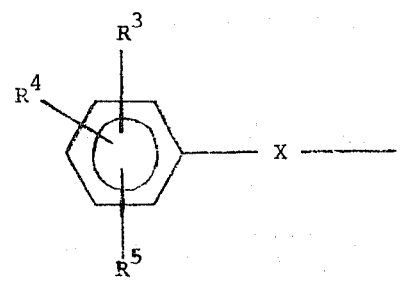

wherein X is selected from the group consisting of

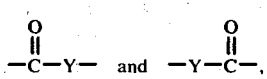

wherein Y is a straight hydrocarbon chain having 2 or 3 carbon atoms, said chain being saturated or containing one double bond and having at most 2 hydrogen atoms substituted by substituents selected from the group consisting of lower alkyl, lower alkenyl, phenyl, phenyl substituted in p-position by lower alkyl, lower alkoxy, halogen (F, Cl, Br) or $CF_3$, benzyl and benzyl substituted in p-position by lower alkyl, lower alkoxy, halogen (F, Cl, Br) or $CF_3$; $R^3$, $R^4$, $R^5$, $R^6$ and $R^7$ are the same or different and are selected from the group consisting of hydrogen, lower alkyl, lower alkenyl, lower alkoxy, hydroxy esterified with phosphoric acid, $OCOR^8$, F, Cl, Br, $CF_3$, $NO_2$,
wherein $R^8$ is
  lower alkyl,
  where M is selected from the group consisting of H, Na, K, ½ Ca, and a pharmaceutically acceptable amine.

46. A method of treating an animal body exposed to exogenous prostaglandins, in order to counteract unfavorable effects of the prostaglandin exposure comprising administration of a therapeutically effective amount of a compound of Formula I to said animal body, Formula I being:

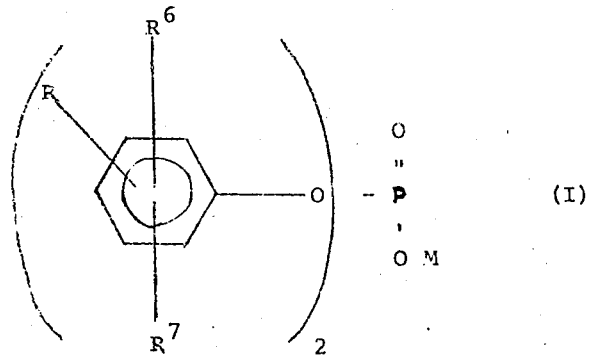

wherein R is positioned in m- or p-position relative to the phosphoric acid ester group and is

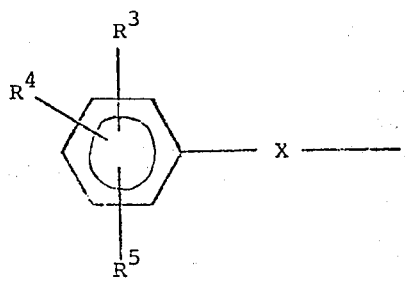

wherein X is selected from the group consisting of -C-Y- and

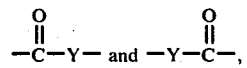

wherein Y is a straight hydrocarbon chain having 2 or 3 carbon atoms, said chain being saturated or containing one double bond and having at most 2 hydrogen atoms substituted by substituents selected from the group consisting of lower alkyl, lower alkenyl, phenyl, phenyl substituted in p-position by lower alkyl, lower alkoxy, halogen (F, Cl, Br) or $CF_3$, benzyl and benzyl substituted in p-position by lower alkyl, lower alkoxy, halogen (F, Cl, Br) or $CF_3$; $R^3$, $R^4$, $R^5$, $R^6$ and $R^7$ are the same or different and are selected from the group consisting of hydrogen, lower alkyl, lower alkenyl, lower alkoxy, hydroxy, hydroxy esterified with phosphoric acid, $OCOR^8$, F, Cl, Br, $CF_3$, $NO_2$,
wherein $R^8$ is
  lower alkyl,
  where M is selected from the group consisting of H, Na, K, ½ Ca, and a pharmaceutically acceptable amine.

* * * * *

UNITED STATES PATENT OFFICE
CERTIFICATE OF CORRECTION

Patent No. 3,991,187    Dated November 9, 1976

Inventor(s) Knut Bertil Hogberg, et al

It is certified that error appears in the above-identified patent and that said Letters Patent are hereby corrected as shown below:

Column 2, line 15; change "debmatitis" to read ---dermatitis---.

Column 3, line 35; change "hve" to read ---have---.

Column 5, line 35; change "$CNR^8COR^8$" to read ---$NR^8COR^8$---.

Column 7, line 17; change "$Cl_3CCH_2OP(O)Cl$" to read

---$Cl_3CCH_2OP(O)Cl_{\underline{2}}$---.

Column 12, line 7; change "methoxy-4-(3-nitrophenyl)" to read
---methoxy-4-(3-(3-nitrophenyl)---.

Column 13, line 38; change "bis(4-(3-aminophenyl)" to read
---bis(4-(3-(3-aminophenyl)---.

Column 14, line 63; after "phosphate" the rest of the line and the next 2 lines must be deleted, they do not appear in specification.

Column 15, line 2; change "hydroxphenyl)" to read---hydroxyphenyl)---.

Column 18, line 1; change "Pd/C C" to read ---Pd/C---.

Column 25, line 42; change "dihydroxy-4-(4-" to read ---dihydroxy-4-(3-(4- ---.

line 50; change "(2,4dihydroxyphenyl)" to read
---(2,4-dihydroxyphenyl)---.

UNITED STATES PATENT OFFICE
CERTIFICATE OF CORRECTION

Patent No. 3,991,187                    Dated November 9, 1976

Inventor(s) Knut Bertil Hogberg, et al

It is certified that error appears in the above-identified patent and that said Letters Patent are hereby corrected as shown below:

Column 25, line 52; change "soium" to read ---sodium---.

Column 26, line 20; change "3methylphenyl)" to read ---3-methylphenyl)---.

line 61; in the Table, change "III Talcum,Ph.Nord 1.5 g." to read ---III Talcum,Ph.Nord 15 g.---.

Column 29, line 45; change "bis(4-(3-(2,4,6-" to read ---bis(4-(3-oxo-3-(2,4,6- ---.

Column 30, Claim 1; just above formula, change "(Claim 70, continued) to read ---(Claim 1, continued)---.

Column 35, line 18; change "alkoxy, hydroxy esterified" to read ---alkoxy, hydroxy, hydroxy esterified---.

Column 36, line 21; delete line "-C-Y-and".

Signed and Sealed this thirtieth Day of August 1977

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,991,187          Dated November 9, 1976

Inventor(s) Knut Bertil Hogberg, et al

It is certified that error appears in the above-identified patent and that said Letters Patent are hereby corrected as shown below:

Col. 21, Line 42; line dropped, add --- The hexaacetate of sodium bis (3,5-dihydroxy-4-(3-(4- hydroxyphenyl)- ---

Col. 21, Line 43; '-propionylphenyl" change to read --- propionyl)phenyl) ---

Signed and Sealed this

Tenth Day of January 1978

[SEAL]

Attest:

RUTH C. MASON
*Attesting Officer*

LUTRELLE F. PARKER
*Acting Commissioner of Patents and Trademarks*